US006756208B2

(12) United States Patent
Griffin et al.

(10) Patent No.: US 6,756,208 B2
(45) Date of Patent: Jun. 29, 2004

(54) PLASMA GLUCOSYLCERAMIDE DEFICIENCY AS RISK FACTOR FOR THROMBOSIS AND MODULATOR OF ANTICOAGULANT PROTEIN C

(76) Inventors: John H. Griffin, 13924 Boquita Dr., Del Mar, CA (US) 92014; Hiroshi Deguchi, 12514 Caminito Mira, Del Mar, CA (US) 92130; Jose Fernandez, 8638 Villa La Jolla Dr., La Jolla, CA (US) 92037

(*) Notice: Subject to any disclaimer, the term of this patent is extended or adjusted under 35 U.S.C. 154(b) by 122 days.

(21) Appl. No.: 10/086,943

(22) Filed: Feb. 28, 2002

(65) Prior Publication Data

US 2002/0177563 A1 Nov. 28, 2002

Related U.S. Application Data

(60) Provisional application No. 60/272,103, filed on Feb. 28, 2001, and provisional application No. 60/278,045, filed on Mar. 22, 2001.

(51) Int. Cl.$^7$ .................. C12Q 1/56; C07H 17/02; A61B 5/02
(52) U.S. Cl. ................. 435/13; 536/17.9; 600/481
(58) Field of Search .............. 435/13; 536/17.9; 600/481

(56) References Cited

FOREIGN PATENT DOCUMENTS

WO    WO 98/56365 A1    12/1998
WO    WO 00/53264 A1    9/2000

OTHER PUBLICATIONS

Debuchi H, Fernandez JA, Pabinger I, Heit JA and Griffin JH. "Plasma Glucosylceramide Deficiency as Potential Risk Factor for Venous Thrombosis and Modulator of Anticoagulant Protein C Pathway." Blood 97: 1907–14, 2001.
Deguchi H, Fernandez JA, and Griffin JH. "Neutral glycosphingolipid–dependent inactivation of coagulation factor Va by activated protein C and protein S." J Biol Chem 277:8861–65, 2002.
Griffin JH, Kojima K, Banka CL, Curtiss LK, Fernandez JA. "High–Density lipoprotein enhancement of anticoagulant activities of plasma protein S and activated protein C." J. Clin Invest. 103:219–227, 1999.
Fernandez JA, Kojima K, Petaja J, Hackeng TM, Griffin JH. "Cardiolipin enhances protein C pathway anticoagulant activity." Blood Cells Mol Dis. 26:115–23, 2000.

Deguchi H, Fernandez JA, Hackeng TM, Banka CL, Griffin JH. "Cardiolipin is a normal component of human plasma lipoproteins." Proc. Natl Acad Sci USA. 97:1743–1748, 2000.
Smirnov MD, Esmon CT. "Phosphatidylethanolamine incorporation into vesicles selectively enhances factor Va inactivation by activated protein C." J Biol Chem. 269:816–819, 1994.
Svensson PJ, Dahlback B. "Resistance to activated protein C as a basis for venous thrombosis." N Engl J. Med. 330:517–522, 1994.
Clarke JTR. "The glycosphingolipids of human plasma lipoproteins." Can J Biochem. 59:412–417, 1981.
Dawson G, Kruski AW, Scanu AM. "Distribution of glycosphinogolipids in the serum lipoproteins of normal human subjects and patients with hypo– and hyperlipidemias." J Lipid Res. 17:125–131, 1976.
Hakomori S, Igarashi Y. "Functional role of glycosphingolipids in cell recognition and signaling." J Biochem. 118:1091–1103, 1995.
Chatterjee S. "Sphingolipids in atherosclerosis and vascular biology." Arterioscler Thromb Vasc Biol. 18:1523–1533, 1998.
Heran, C. et al., Antithrombotic efficacy of RPR208566, a novel factor Xa inhibitor, in a rat model of carotid artery thrombosis. Eu. J. Pharm. 389:201–207 2000.
Phillips, D. J. et al., Protein S, an antithrombotic factor, is synthesized and released by neural tumor cells. J. Neurochem. 61:344–347 1993.

*Primary Examiner*—Kathleen K. Fonda
(74) *Attorney, Agent, or Firm*—Morgan & Finnegan, L.L.P.

(57) ABSTRACT

The present invention has determined that exogenously added glucosylceramide (GlcCer) and other neutral glycolipids such as the homologous Glc-containing globotriaosylceramide (Gb3Cer), dose-dependently prolonged clotting times of normal plasma in the presence but not absence of APC:protein S, indicating GlcCer or Gb3Cer can enhance protein C pathway anticoagulant activity. In studies using purified proteins, inactivation of factor Va by APC:protein S was enhanced by GlcCer alone and by GlcCer, globotriaosylceramide, lactosylceramide, and galactosylceramide in multicomponent vesicles containing phosphatidylserine and phosphatidylcholine. Thus, the present invention provides neutral glycolipids such as GlcCer and Gb3Cer, as anticoagulant cofactors that contribute to the antithrombotic activity of the protein C pathway. The present invention has also determined that a deficiency of plasma GlcCer is a risk factor for thrombosis. Methods are provided to determine individuals at risk for thrombosis, methods of treatment as well as methods of screening for antithrombotic factors from neutral glycolipids.

12 Claims, 9 Drawing Sheets

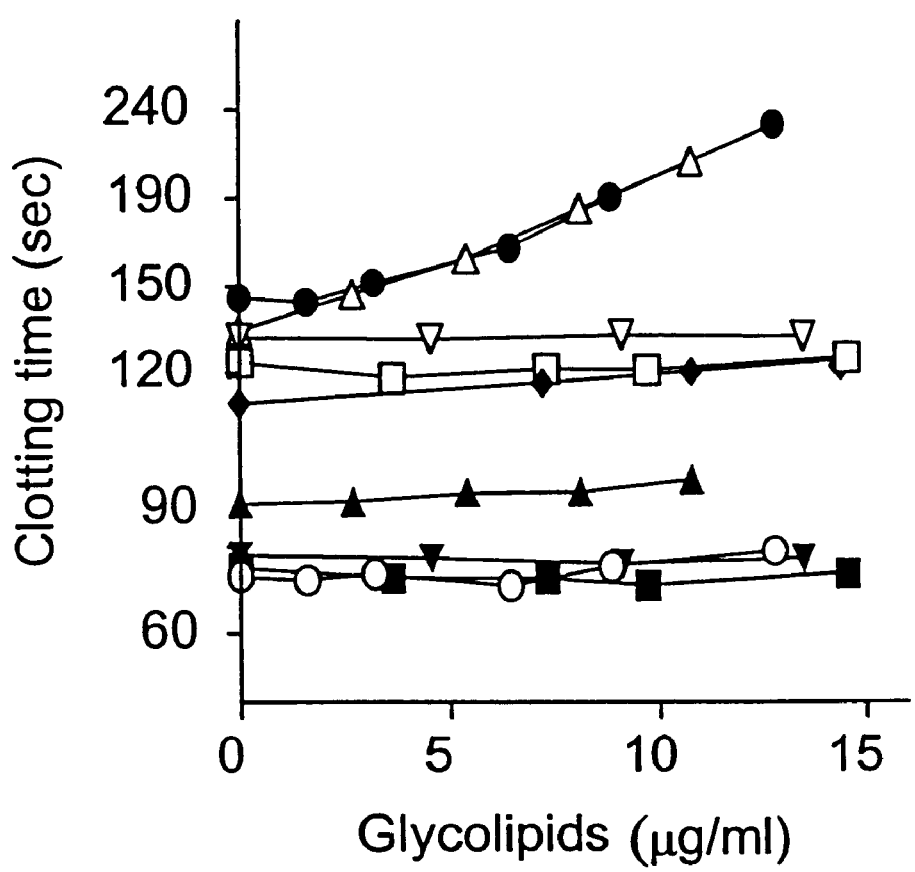

PLASMA GLUCOSYLCERAMIDE DEFICIENCY AS RISK FACTOR FOR THROMBOSIS AND MODULATOR OF ANTICOAGULANT PROTEIN C

This application claims benefit to Provisional Application No. 60/272,103, filed Feb. 28, 2001, and Provisional Application No. 60/278,045, filed Mar. 22, 2001.

This project has been funded at least in part with Federal funds from the Department of Health and Human Services under NIH Grant HL 21544.

FIELD OF THE INVENTION

The present invention relates to neutral glycolipids as antithrombotic factors for prevention or inhibition of thrombosis and as anti-inflammatory agents. More specifically the invention relates to neutral glycolipids such as glucosylceramide, globotriaosylceramide, galactosylceramide, lactosylceramide and the like as antithrombotic factors and the use of the neutral glycolipids for prevention or inhibition of thrombosis and as anti-inflammatory agents. The present invention also relates to methods for screening for individuals at risk of thrombosis and relates to methods of screening for antithrombolytic agents from candidate neutral glycolipids.

BACKGROUND OF THE INVENTION

Poor anticoagulant response to activated protein C (APC), termed APC resistance, is detected in 20 to 50% of venous thrombosis patients, (1) and it can be present in patients with normal factor V genotype (2–4) or with the factor V polymorphism, arginine to glutamine substitution at amino acid 506, (5–7) or with a variety of acquired conditions, eg., oral contraceptive use, (8) autoantibody against APC, (9) etc. APC resistance is also associated with increased risk of ischemic stroke in subjects with normal R506-factor V. (10, 11) Severe deficiency of protein C or protein S causes life-threatening thrombosis. (12–15) Thus, the protein C pathway provides a major physiologic anticoagulant mechanism for down-regulation of thrombin generation in which APC proteolytically inactivates factors Va and VIIIa. (16)

Blood coagulation reactions are stimulated by phospholipid membrane surfaces as is the anticoagulant protein C pathway. (17) However, procoagulant and anticoagulant complexes may be differentially affected by different membrane phospholipid components. (18–20) Because we found that high density lipoprotein (HDL) exhibits anticoagulant cofactor activity for APC:protein S (21) we decided to evaluate further the influence of plasma lipids and lipoproteins on the protein C pathway.

Plasma lipoproteins contain glycolipids as well as phospholipids. (22–24) Glycolipids can play critical roles as bioregulators of a variety of processes such as cell proliferation, cell mobility and apoptosis. (23) Glycolipid molecules present their highly varied saccharide residues on the surface of lipoprotein particles as well as on cell surfaces, exposing saccharides to interactions with other cells, antibodies, bacterial toxins, and viral envelope proteins. (23) Several hundred glycolipids are known. However, the relevance of glycolipids to the blood coagulation system is currently unknown. Studies of the relationship between glycolipids and risks of venous thrombosis or of the influence of glycolipids on the APC:protein S anticoagulant pathway have not been reported.

This present invention demonstrates the relationship between thrombosis and plasma levels of neutral glycolipids. The present invention demonstrates that a neutral glycolipid deficiency is a potential risk factor for thrombosis and gives rise to the novel broad concept that neutral glycolipids may contribute to regulation of thrombin generation, blood coagulation, thrombosis and inflammation.

SUMMARY OF THE INVENTION

One object of the invention is to provide a neutral glycolipid as an antithrombotic or anti-inflammatory factor.

Another object of the invention is to provide a neutral glycolipid having the formula: R—sugar-linked ceramide as an antithrombotic or anti-inflammatory factor.

The invention further provides pharmaceutical compositions comprising neutral glycolipids, alone or in combination with at least one anticoagulant, antithrombotic agent, thrombolytic agent, antiplatelet drug, anti-inflammatory drug, high density lipoprotein or portion thereof, or combinations thereof.

The present invention provides neutral glycolipids in vesicle form alone or in combination with one or more lipids to form an antithrombotic or anti-inflammatory vesicle. The vesicles may be provided in the form of a pharmaceutical composition alone or in combination with at least one anticoagulant, antithrombotic agent, thrombolytic agent, antiplatelet drug, anti-inflammatory drug, high density lipoprotein or portion thereof, or combinations thereof.

The invention further provides nutritional supplements or dietary supplements comprising one or more neutral glycolipids and/or one or more vesicles comprising one or more neutral glycolipids.

The present invention provides a method of determining an individual at risk for thrombosis by determination of a below-normal level of a neutral glycolipid in a biological specimen, a below-normal level indicative of a risk factor for thrombosis in the individual.

The invention further provides a method of determining a neutral glycolipid concentration in a biological specimen.

Another aspect of the invention is a method of enhancing antithrombotic or anti-inflammatory activity in a subject comprising administration of at least one neutral glycolipid.

The invention further relates to a method for screening for candidate neutral glycolipids having antithrombotic activity.

The invention further provides an animal model for thrombosis comprising an animal deficient in glucosylceramide.

BRIEF DESCRIPTION OF THE DRAWINGS

These and other objects, features, and many of the attendent advantages of the invention will be better understood upon a reading of the following detailed description when considered in connection with the accompanying figures:

FIG. 1A: GlcCer levels in 70 venous thrombosis patients and 70 controls (p=0.0007);

FIG. 1B: GlcCer levels for patients and controls who are less than 45 years old (p=0.0003);

FIG. 1C: GlcCer levels for patients and controls $\geq 45$ years old (p=0.33);

FIG. 1D: PE levels for 70 venous thrombosis patients and 70 controls (p=0.48).

FIG. 3. Anticoagulant response of plasma to APC:protein S is enhanced by addition of GlcCer and globotriaosylceramide (Gb3Cer). Glycolipids were added to normal plasma aliquots that were then assayed using the dilute modified prothrombin time assay as described in the presence and absence of APC:protein S. Clotting times are shown for the presence of APC:protein S (● indicates GlcCer; Δ, Gb3Cer;, galactosylceramide (GalCer); and ▽, lactosylceramide (LacCer)) and for baseline controls (without APC or protein S added) (○ indicates GlcCer; ▲, Gb3Cer; ■, GalCer; and ▼, LacCer). For GlcCer addition, clotting times are also shown for addition of APC alone (♦ indicates GlcCer).

FIG. 4A: PT in the presence of added APC:protein S for venous thrombosis patients (excluding those with Gln506-factor V);

FIG. 4B: PT in the presence of added APC:protein S for controls (excluding those with Q506-factor V);

FIG. 4C: Baseline PT for thrombosis patients;

FIG. 4D: Baseline PT for control subjects.

(FIG. 5A) Time course for factor Va (1.5 nM) inactivation by APC (6 nM final) and protein S (18 nM final) in the presence of 5 mM $CaCl_2$ and GlcCer (●) or PC vesicles (○) (21.5 μM) or buffer (×) at 37° C. Controls without APC:protein S included GlcCer (Δ) or PC vesicles (*). The factor Va activity observed at 0 time was defined as 100%.

(FIG. 5B) For studies using multicomponent vesicles, various concentrations of PC (○), PC/GlcCer (●), PC/PS (Δ) and PC/PS/GlcCer (▲) vesicles were incubated with APC (1 nM final), protein S (18 nM final), and factor Va (1.5 nM final) for 3 min at 37° C., and then residual factor Va was determined. The factor Va activity observed with no lipid vesicles added was defined as 100%.

FIG. 6A GlcCer,

FIG. 6B GalCer,

FIG. 6C LacCer,

FIG. 6D Gb3Cer and

FIG. 6E globotetraosylceramide (Gb4Cer). Content of glycolipid: (●)=0%; (○)=1%; (Δ)=5%; (▲)=10%.

DETAILED DESCRIPTION OF THE INVENTION

Figure 1A:
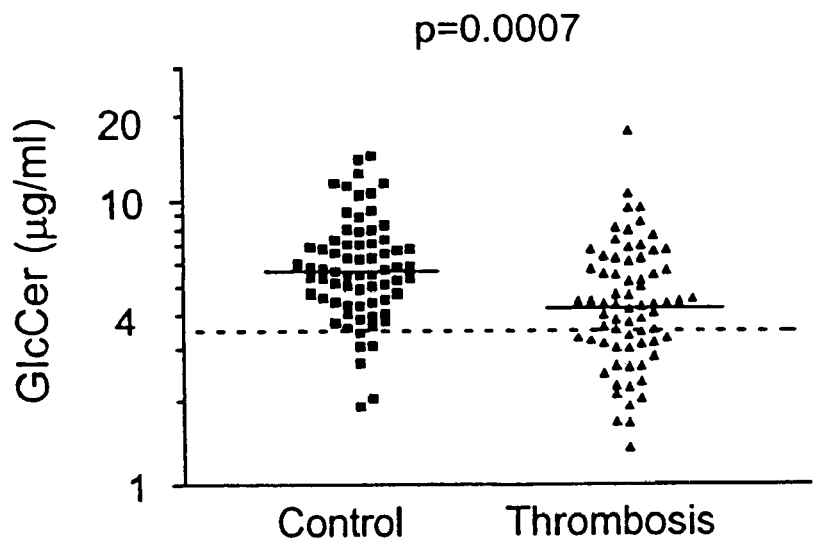
FIGS. 1A–1D. Plasma glucosylceramide (GlcCer) levels are low in venous thrombosis patients. Plasma GlcCer and phosphatidylethanolamine (PE) were quantitated using HPLC for 70 venous thrombosis patients and 70 controls. Solid lines indicate mean values from analysis of the distribution of log-transformed data and the dashed line in panel A indicates the $10^{th}$ percentile value for controls.

The present invention are novel antithrombotic factors that contribute to regulation of thrombin generation, blood coagulation and thrombosis and act as anti-inflammatory agents. The novel antithrombotic factor of the present invention participates with activated protein C and protein S in prolongation of clotting times. The antithrombotic factor of the present invention enhances factor Va inactivation by activated protein C and protein S thus inhibiting the formation of thrombin.

The novel antithrombotic factor of the present invention comprise one or more neutral glycolipids, in particular, neutral glycosphingolipids. The neutral glycolipids of the present invention have no net charge. The neutral glycolipids of the present invention have one or more sugars in their head group connected directly or covalently to the —OH at C-1 of a ceramide moiety.

The neutral glycolipids of the present invention comprise the general formula:

R—sugar-linkage-ceramide. The sugar moiety is preferably a hexose sugar selected from the group including but not limited to glucose, galactose, allose, altrose, mannose, gulose, idose, talose and the like, preferably glucose or galactose. The linkage to ceramide is a direct or covalent linkage between the sugar and ceramide, preferably a beta-1 linkage of the sugar moiety to ceramide. The R group is hydrogen (H), or one or more saccharide units. The multiple saccharide units or oligosaccharides, may be various combinations of saccharides or may be repeating units of the same saccharide. The number of saccharide units may be 1 to about 20, preferably 1 to about 6, more preferably 1 to about 3. The saccharide units may be linear or complexed branched units. The saccharide units for position R include but are not limited to galactose, allose, altrose, mannose, gulose, idose, talose and the like, provided the net charge of the glycolipid remains neutral and the neutral glycolipid maintains antithrombotic activity.

Specific embodiments of the general formula of neutral glycolipids of the present invention include but are not limited to glucosylceramide (GlcCer), globotriaosylceramide (Gb3Cer), lactosylceramide (LacCer) galactosylceramide (GalCer) and the like.

The linkage of the saccharide units to the sugar moiety may vary, provided the neutral glycolipid retains the proper conformation to function as an antithrombotic factor. In one embodiment Gb3Cer has the linkage Galα1, 4Galβ1, 4Glc/β1-Cer. In another embodiment, LacCer has the linkage Galβ1, 4Glcβ1-Cer. In yet another embodiment GalCer has the linkage Gal1-Cer.

The fatty acid side chain of the ceramide may vary and may be saturated, monounsaturated or polyunsaturated. The number of carbon atoms in the fatty acid chain may vary and may include, for example 16, 18, 22 or 24 carbon atoms, provided the polar head groups of OH at C-3 and amide group at C-2 of ceramide is maintained.

Sugars and saccharides of the neutral glycolipid that may be used in the present invention that contribute to the antithrombotic activity of the neutral glycolipid include but are not limited to glucose, galactose, lactose, globotriose, erythrose, threose, ribose, arabinose, xylose, lyxose, allose, altrose, mannose, gulose, idose, talose, sedoheptose, sedoheptulose and the like. The sugars may be in the D-isomer form or L-isomer form, preferably D-isomers.

The neutral glycolypids for use in the present invention may be prepared by standard methods known in the art. The neutral glycolipids may be purified from biological sources or prepared biosynthetically by methods known in the art, or obtained through commercial sources. For galactosylceramide a preferred commercial source is Sigma Chemical Company, St. Louis, Mo. The neutral glycolipids should be greater than about 90% pure, preferably about 95% or greater purity, more preferably greater than 98% pure.

The neutral glycolipids of the present invention may be provided in vesicle or bilayer form alone or with one or more lipids added. The lipids may include, but are not limited to one or more sphingolipids, phosphatidylserine, phosphatidylcholine, phosphatidylethanolamine, cholesterol, cholesterol ester, triglyceride, diacylglyceride, lecithin, liposomes and the like, and combinations thereof. The neutral glycolipid comprises about 1% to about 100% of the total components of the vesicle, preferably about 1% to about 50% of the total components, more preferably about 1% to about 10% of the total components. One or more lipids comprise the remainder of the components.

In one embodiment of the present invention, the antithrombotic factor vesicle comprises a neutral glycolipid, alone. In another embodiment of the antithrombotic vesicle, the vesicle comprises one or more various neutral glycolipids and sphingomyelin. In yet another embodiment of the antithrombotic factor vesicle, the vesicles comprise one or more various neutral glycolipids, phosphatidylethanolamine and cholesterol.

Another embodiment of the antithrombotic vesicle, the vesicle comprises one or more neutral glycolipids and cholesterol. In another embodiment, the vesicle comprises one or more neutral glycolipids, sphingomyelin and cholesterol.

In one embodiment, the antithrombotic vesicle comprises glucosylceramide, phosphatidylcholine and phosphatidylserine. In another embodiment, the anticoagulant cofactor vesicle comprises globotriaosylceramide, phosphatidylcholine and phosphatidylserine. Another embodiment includes a vesicle comprising lactosylceramide, phosphatidylcholine and phosphatidylserine.

In yet another embodiment, the antithrombotic vesicle comprises glucosylceramide, sphingomyelin and cholesterol. Another embodiment of the vesicle comprises globotriaosylceramide, sphingomyelin and cholesterol. In yet another embodiment of the antithrombotic vesicle, the vesicle comprises lactosylceramide, sphingomyelin and cholesterol.

The ratios of each component in the vesicle may be varied to achieve optimal antithrombotic activity. In an embodiment of the multicomponent antithrombotic vesicle the percentage of one or more neutral glycolipids in the multicomponent vesicle may range from about 1% to about 99%, preferably about 1% to about 50%, more preferably about 1% to about 25% weight/total weight of vesicle. In another embodiment the percentage of neutral glycolipid in the multicomponent vesicle is about 1% to about 10%, phosphatidylcholine is in a range of about 80 to about 99% and phosphatidylserine is in a range of about 0 to about 10% (weight/weight). In one particular embodiment, the ratio of glucosylceramide to phosphatidylcholine to phosphatidylserine ratios are 80%: 10%: 10% (weight/weight). Other ratios may be used as well as various combinations of neutral glycolipids and various combinations of lipids provided the vesicle has antithrombotic activity. The vesicles may be made by methods known in the art such as those described in U.S. Pat. Nos. 5,783,210; 5,540,936; and 5,429,823, and the like.

One or more of the novel antithrombotic factors of the present invention may be provided in the form of a pharmaceutical composition along with a pharmaceutically acceptable carrier or exipient. In one embodiment, the pharmaceutical composition comprises one neutral glycolypid or a combination of neutral glycolipids with a pharmaceutically acceptable carrier. In another embodiment, the pharmaceutical composition comprises a neutral glycolipid selected from the group consisting of glucosylceramide, globotriaosylceramide, galactosylceramide, lactosylceramide, or combinations thereof and a pharmaceutically acceptable carrier.

The antithrombotic factor may be provided in the pharmaceutical composition in any concentration sufficient to cause or enhance antithrombotic activity, in particular, to cause or enhance the anticoagulant activity of activated protein C and/or protein S. In one embodiment, the antithrombotic factor is present in the pharmaceutical composition in a concentration of about 0.01 $\mu$g/ml to about 1 mg/ml, preferably about 0.05 $\mu$g/ml to about 50 $\mu$g/ml, more preferably, about 0.05 $\mu$g/ml to about 25 $\mu$g/ml.

In another embodiment, the neutral glycolypid is present in the pharmaceutical composition in an amount sufficient to increase the circulating blood level of neutral glycolypid in a subject, including a human subject, by at least about 0.1 $\mu$g/ml to about 15 $\mu$g/ml, preferably about 0.5 $\mu$g/ml to about 10 $\mu$g/ml, more preferably about 1.0 $\mu$g/ml to about 7 $\mu$g/ml.

The present invention also provides nutritional compositions or nutritional supplements comprising one or more neutral glycolipids sufficient to increase the circulating blood level by at least about 0.1 $\mu$g/ml to about 15 $\mu$g/ml, preferably about 0.5 $\mu$g/ml to about 10 $\mu$g/ml, more preferably about 1.0 $\mu$g/ml to about 7 $\mu$g/ml. The neutral glycolipid may be provided alone as a dietary supplement or may be provided in combination with other active ingredients such as conventional vitamin and/or mineral supplements. Food sources may be supplemented with one or more neutral glycolipids for proper maintenance or elevation of neutral glycolipids in a subject. For parenteral nutrition, one or more neutral glycolipids may be added to foodstuffs including but not limited to cereals, milk (liquid and powdered), milk-derived products such as butter, cheese, yogurt, and the like, infant formula, flour, grain and grain mixtures, such as wheat, oats, rice, barley and the like, sugar, sugar substitutes, eggs, egg supplements and the like. The nutritional supplement may be in any form such as a capsule, tablet, powder, gel, suspension and the like. The nutritional supplement is provided in a dose of about 1 mg/day to about 500 mg/day of neutral glycolipid, preferably about 2 mg/day to about 20 mg/day of neutral glycolipid to a subject.

The pharmaceutical composition may also comprise other active ingredients, such active ingredients include but are not limited to anticoagulants, antithrombotics, thrombolytic agents, antiplatelet drugs, anti-inflammatory drugs, high density lipoprotein or portions thereof, and combinations thereof.

In pharmaceutical compositions, thrombolytic agents which may be used in combination with one or more neutral glycolipids include but are not limited to tissue plasminogen activator (tPA) or its analogs, urokinase or its analogs, prourokinase or its analogs, streptokinase or its analogs, an acylated form of plasminogen or plasmin or their analogs, acylated streptokinase-plasminogen complex and the like.

Anticoagulants which may be used in combination with a neutral glycolipid include but are not limited to plasma-derived protein C, recombinant protein C, or modified protein C; plasma-derived activated protein C, recombinant or modified activated protein C (APC), wherein modified forms have appropriate biological properties; Protein S, recombinant Protein S, one or more of the chemically synthesized domains of Protein S; example the GLA domain constructs containing the Gla domain, and one or more of the four EGF-like domains linked to the Gla-TSR domains; tissue factor pathway inhibitor (TFPI), antithrombin III (ATIII); warfarin; heparin; glycosaminoglycan; soluble thrombomodulin; soluble endothelial protein C receptor and the like.

Antiplatelet agents which may be used in combination with a neutral glycolipid include but are not limited to aspirin, dipyridamole, clopidogrel, abciximab (Reopro™) or any inhibitor of platelet glycoprotein IIb–IIIa or any inhibitor of ADP receptors.

Anti-inflammatory agents which may be used in combination with a neutral glycolipid antithrombotic of the present invention include but are not limited to Aminoarylcarboxylic Acid Deriviatives such as Etofenamate, Meclofenamic Acid, Mefanamic Acid, Niflumic Acid, Arylacetic Acid Derivatives such as Acemetacin, Amfenac, Cinmetacin, Clopirac, Diclofenac, Fenclofenac, Fenclorac, Fenclozic Acid, Fentiazac, Glucametacin, Isoxepac, Lonaolac, Metiazinic Acid, Oxametacine, Proglumetacin, Sulindac, Tiaramide, Tolmetin, Arylbutyric Acid Derivatives such as, Butibufen, Fenbufen, Arylcarboxylic Acids such as Clidanac, Ketorolac, Tinoridine, Arylpropionic Acid Derivatives such as Bucloxic Acid, Carprofen, Fenoprotein, Flunoxaprotein, Ibuprofen, Ibuproxam, Oxaprozin, Piketoprofen, Pirprofen, Pranoprofen, Protizinic Acid, Tiaprofenic Acid, Pyrazoles such as Mepirizole, Pyrazolones such as Clofezone, Feprazone, Mofebutazone, Oxyphenbutazone, Phenylbutazone, Phenyl Pyrazolidininones, Suxibuzone, Thiazolinobutazone, salicylic Acid Derivatives such as Bromosaligenin, Fendosal, Glycol Salicylate, Mesalamine, 1-Naphthyl Salicylate, Olsalazine, Sulfasalazine, Thiazinine-caroboxamides such as Droxicam, Isoxicam, Piroxicam, epsilon-Acetamidocaproic Acid, S-Adenosylmethionine, 3-Amino-4-hydroxybutyric Acid, Amixetrine, Bendazac, Bucolome, Carbazones, Difenpiramide, Ditazol, Guaiazulene, Ileterocylic Aminoalkyl Esters of Mycophenolic Acid and derivatives, Nabumetone, Nimesulide, Orgotein, Oxaprol, Oxazole Derivatives, Paranyline, Pifoxime, 2-substituted-4,6-ditertiary-butyl-S-hydroxyl-1,3-pyrimidines, Proquazone, Sialyl Lewis.sup.x Dimers, or Tenidap and the like. Additional therapeutic agents include any COX-2 inhibitor, any selective estrogen-receptor modifier (SERM) such as raloxifene, and any inhibitor of HMG-CoA reductase. Additional therapeutic agents which can be administered include steroids for example, glucocorticoids such as predisone, methyl prednisolone, dexamethasome and the like.

High Density Lipoprotein (HDL) and portions thereof can be used in combination with one or more antithrombotic neutral glycolipids include but are not limited to apolipoprotein A-II, apolipoprotein A-II, apolipoprotein B48, apolipoprotein B100, apolipoprotein C-I, apolipoprotein C-II, apolipoprotein C-III, apolipoprotein D, apolipoprotein E, apolipoprotein H, apolipoprotein J, apolipoprotein M, and combinations thereof, and the like.

In regard to the use of neutral glycolipids in combination with APC, APC is a very species specific moiety. The dosage for human or recombinant human APC in a human is much lower than the appropriate dosage in a mouse, for example. The normal baseline level of APC in a human is typically about 2.2 ng/ml of blood. In practice of the invention methods, it is necessary to administer sufficient APC to raise the blood level slightly above the baseline level, but not so much as to risk causing undesirable bleeding. A therapeutically effective amount of human APC is typically administered to a human at a dosage sufficient to raise the blood level of APC by from about 1.0 ng/ml to about 500 ng/ml, preferably, from about 5 ng/ml to about 200 ng/ml.

The APC is preferably administered parenterally to ensure its delivery into the bloodstream in an effective form by injecting the appropriate dose as continuous infusion for about 4 to about 96 hours prior to, concurrently with or after administration of neutral glycolipids. Preferably, the appropriate dose of APC will be administered by continuous infusion for about 4 to about 72 hours. More preferably, the appropriate dose of APC will be administered by continuous infusion for about 4 to about 48 hours. More preferably, the appropriate dose of APC will be administered by continuous infusion for about 12 to about 48 hours. More preferably, the appropriate dose of APC will be administered by continuous infusion for about 4 to about 36 hours. More preferably, the appropriate dose of APC will be administered by continuous infusion for about 12 to about 24 hours. Most preferably, the appropriate dose of APC will be administered by continuous infusion for about 24 hours. The administration of APC will begin as soon as possible following diagnosis of the vascular occlusive or arterial thromboembolic disorder. An appropriate loading dose of APC may be given by bolus injection with or without subsequent APC infusion.

The amount of APC administered can be from about 0.01 mg/kg/hr to about 0.10 mg/kg/hr which is equivalent to about 17 mg/70 kg/24 hours to about 170 mg/70 kg/24 hours. While the dose level is identified as a specific amount per 24 hours, one skilled in the art would recognize that this is a designation of the dose level and is not necessarily limited to a 24 hour infusion but may include continuous infusion for various times, for example, from about four hours to about ninety-six hours. More preferably, the amount of APC administered is about 0.01 mg/kg/hr to about 0.05 mg/kg/hr (about 17 mg/70 kg/24 hours to about 84 mg/70 kg/24 hours). While more preferably the amount of APC administered will be about 0.01 mg/kg/hr to about 0.03 mg/kg/hr (about 17 mg/70 kg/24 hours to about 50 mg/70 kg/24 hours). Furthermore, the amount of APC administered is from about 0.02 mg/kg/hr to about 0.05 mg/kg/hr which is equivalent to about 34 mg/70 kg/24 hours to about 84 mg/70 kg/24 hours. More preferably, the amount of APC administered is about 0.024 mg/kg/hr to about 0.048 mg/kg/hr (about 40 mg/70 kg/24 hours to about 80 mg/70 kg/24 hours). While more preferably the amount of APC administered will be about 0.027 mg/kg/hr to about 0.045 mg/kg/hr (about 45 mg/70 kg/24 hours to about 75 mg/70 kg/24 hours). While more preferably the amount of APC administered will be about 0.030 mg/kg/hr to about 0.042 mg/kg/hr (about 50 mg/70 kg/24 hours to about 70 mg/70 kg/24 hours). While more preferably the amount of APC administered will be about 0.033 mg/kg/hr to about 0.039 mg/kg/hr (about 55 mg/70 kg/24 hours to about 65 mg/70 kg/24 hours). Preferable amounts of APC administered are about 0.024 mg/kg/hr (about 40 mg/70 kg/24 hours), about 0.027 mg/kg/hr (about 45 mg/70 kg/24 hours) or, about 0.030 mg/kg/hr to about 0.042 mg/kg/hr (about 50 mg/70 kg/24 hours). Clearly, the amount of APC can be reduced when administered with a co-factor such as Protein S.

Alternatively, the APC will be administered by injecting a portion of the appropriate dose per hour as a bolus injection over a time from about 5 minutes to about 120 minutes, followed by continuous infusion of the appropriate dose for about twenty three hours to about 96 hours which results in the appropriate dose administred over 24 hours to 96 hours.

The most preferably dose level of APC to be administered for thrombotic occlusion (e.g. stroke) as described herein will be about 0.024 mg/kg/hr (U.S. Pat. No. 5,084,274).

The protein S may be provided in a concentration range to achieve an increase in the circulating blood level of protein S in a subject by about 0.1 to about 20 $\mu$g/ml, preferably about 1 to about 10 $\mu$g/ml, more preferably about 2 to about 5 $\mu$g/ml.

The antithrombotic vesicles may also be provided in the form of a pharmaceutical composition along with a pharmaceutically acceptable carrier.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, vaginal or rectal means.

In addition to the active ingredients, the pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth, and proteins such as gelatin and collagen. If desired, disintegrating or solubilizing agents may be added, such as the cross-linked polyvinylpyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of a anticoagulant cofactor, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, a therapeutically effective dose can be estimated initially by determination of the ability of the dose to enhance APC anti-coagulant activity An animal model may also be used to determine the appropriate concentration range and route of administration. Such information can then be used as a guide or reference for determining useful doses and routes for administration in humans bearing in mind that some anti-coagulant factors such as APC, have been found to be species specific in which optimal doses of APC in humans were lower than those in animals. (U.S. Pat. No. 6,008,199). In clotting assays, Romisch et al (*Fibrinolysis* 1991, 5:191–6) showed that human APC was 20 fold less active in rat plasma than in human plasma as an anticoagulant.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 300 microgram, up to a total dose of about 300 mg, depending upon the route of administration and the specific neutral glycolipid administered. Guidance as to particular dosages and methods of delivery is provided in the literature and generally available to practitioners in the art. In one embodiment, dosages of the antithrombitic cofactor from about 300 µg to about 45 mg, and preferably from about 2 mg to about 20 mg are expected to induce a biological effect. These doses are based on a 70 kg subject. The dosage is an amount sufficient to give an increase in circulating neutral glycolipid concentration of about 0.01 µg/ml to about 15 µg/ml.

The present invention provides a method for determining a neutral glycolipid level or concentration in a biological specimen such as biological fluid, cell or tissue extract comprising isolation of the neutral glycolipid from the biological fluid and measuring the level or concentration of the neutral glycolipid. Quantitation of the concentration of neutral glycolipid is determined in comparison with reference neutral glycolipid standards. The biological fluid includes plasma, serum, lung fluid, saliva, cerebrospinal fluid, lymph, urine, semen, saliva and the like.

In another embodiment, the present invention provides a method for determining a neutral glycolipid concentration in a biological fluid comprising extraction of glycolipids from the biological fluid to form a glycolipid extract, isolation of a specific neutral glycolipid such as glucosylceramide, globotriaosylceramide, lactosylceramide, galactosylceramide and the like from the glycolipid extract followed by determination of the level or concentration of neutral glycolipid by comparison to reference neutral glycolipid standards.

The glycolipids may be extracted from the biological fluid by using methods known in the art employing organic solvents such as chloroform and methanol, or other solvent combinations known to those skilled in the art.

Isolation of the neutral glycolipids such as glucosylceramide, globotriaosylceramide, lactosylceramide, galactosylceramide and the like may be accomplished using high performance liquid chromatography (HPLC), thin layer chromatography (TLC), affinity chromatography using reagents such as verotoxin or shigatoxin and the like, immunoaffinity chromatography and the like. Detection and quantitation may be accomplished by evaporative light scatter detection, mass spectroscopy, or other analytical methods known to those in the art.

In one embodiment, isolation of glucosylceramide is accomplished using a silica-containing column for HPLC such as µPorosil HPLC. The silica bead may have a particle size of about 10 microns and a pore size of about 125 Angstroms.

Antibodies against anticoagulant cofactor glycolipids are useful in the present invention in immunoaffinity chromatography for isolation of anticoagulant cofactor glycolipids and in assays for detection of anticoagulant cofactor glycolipids, for diagnosis of conditions or diseases characterized by altered expression of anticoagulant cofactor glycolipids, and in assays to monitor the efficacy of treatment of patients being treated with a anticoagulant cofactor glycolipid.

Antibodies specific for an anticoagulant cofactor glycolipid may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with a glycolipid which has immunogenic properties. Depending on the host species, various adjuvants may be used to increase immunological response. Such adjuvants include, but are not limited to, Ribi adjuvant R700 (Ribi, Hamilton, Mont.), incomplete Freund's adjuvant, mineral gels such as aluminum hydroxide, and surface active substances such as lysolecithin, pluronic polyols, polyanions, peptides, oil emulsions, keyhole limpet hemocyanin (KLH), and dinitrophenol. Among adjuvants used in humans, BCG (bacillus Calmette Guérin) and *Corynebacterium parvum* are especially preferable.

An anticoagulant cofactor glycolipid may be coupled with a carrier protein such as keyhole limpet hemocyanin (KLH), bovine serum albumin (BSA) and the like to boost an immune response to the anticoagulant cofactor glycolipid to generate anti-glycolipid antibody.

Monoclonal antibodies to a anticoagulant cofactor glycolipid may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) *Nature* 256:495–497; Kozbor, D. et al. (1985) *J. Immunol. Methods* 81:31–42, Cote, R. J. et al. (1983) *Proc. Natl. Acad. Sci.* 80:2026–2030; Cole, S. P. et al. (1984) *Mol. Cell Biol.* 62:109–120).

In addition, techniques developed for the production of "chimeric antibodies," the splicing of mouse antibody genes to human antibody genes to obtain a molecule with appropriate antigen specificity and biological activity can be used (Morrison, S. L. et al. (1984) *Proc. Natl. Acad. Sci.* 81:6851–6855; Neuberger, M. S. et al. (1984) *Nature* 312:604–608; Takeda, S. et al. (1985) *Nature* 314:452–454). Alternatively, techniques described for the production of single chain antibodies may be adapted, using methods known in the art, to produce an anticoagulant cofactor glycolipid specific single chain antibodies. Antibodies with related specificity, but of distinct idiotypic composition, may be generated by chain shuffling from random combinatorial immunoglobulin libraries (Burton D. R. (1991) *Proc. Natl. Acad. Sci.* 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) *Proc. Natl. Acad. Sci.* 86:3833–3837; Winter, G. et al. (1991) *Nature* 349:293–299).

Antibody fragments which contain specific binding sites for a glycolipid may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse, W. D. et al. (1989) *Science* 254.1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between a glycolipid and its specific antibody. A two-site, monoclonal-based immunoassay utilizing monoclonal antibodies reactive to two non-interfering glycolipid epitopes is preferred, but a competitive binding assay may also be employed (Maddox, supra).

Antibody against a glycolipid may be used in immunoaffinity chromatography to isolate the glycolipid from a biological sample, such as plasma. In an immunoaffinity chromatographic procedure, the column material is synthesized by covalently coupling the antibody to an insoluble matrix. The matrix material, alone, should be a substance that itself does not absorb molecules to any significant extent and that has a broad range of chemical, physical and thermal stability. The antibody coupled column material is able to specifically absorb the glycolipid from a solution. Elution occurs by changing the conditions to those in which binding will not occur (alter pH, ionic strength, temperature, and the like.)

A variety of protocols including ELISA, RIA, and FACS for measuring an antigenic substance are known in the art and provide a basis for detection and/or diagnosing altered or abnormal levels of an anticoagulant cofactor glycolipid. Normal or standard values for glycolipid expression are established by combining body fluids or cell extracts taken from normal mammalian subjects, preferably human, with antibody to the glycolipid under conditions suitable for complex formation. The amount of standard complex formation may be quantified by various methods, but preferably by photometric means. Quantities of the glycolipid expressed in subject samples, control samples and test samples from biopsied tissues are compared with the standard values. Deviation between standard and subject values establishes the parameters for diagnosing a neutral glycolipid deficiency, for determining an individual at risk of thrombosis and for monitoring therapeutic treatment.

The above methods are useful in determining various neutral glycolipid deficiencies such as a glucosylceramide deficiency in an individual, useful in identifying individuals in need of neutral glycolipid therapy, and useful in monitoring the efficacy of such therapy.

The present invention provides a method of determining individuals at risk for thrombosis which comprises measuring levels of a neutral glycolipid, in particular, glucosylceramide, in test biological specimen, in particular in plasma or serum, obtained from an individual and comparing the level of the neutral glycolipid such as glucosylceramide to a mean normal range of neutral glycolipid in the normal biological specimen such as plasma or serum. An individual having a lower than normal level or deficiency in glucosylceramide is indicative of a risk factor for thrombosis in the individual.

In one embodiment, a normal range of plasma glucosylceramide is about 4.6 to about 9.7 µg/ml.

In another embodiment, normal mean level of plasma glucosylceramide is about 6.0 µg/ml to 7.0 µg/ml.

In another embodiment, a level of glucosylceramide below the 15$^{th}$ percentile of the normal range is considered a below-normal range, preferably a level of glucosylceramide below the 10$^{th}$ percentile of the mean normal range is considered a below-normal level of glucosylceramide.

Below the 15$^{th}$ percentile of the normal mean range of glucosylceramide considered to constitute a glucosylceramide deficiency represents a plasma concentration of glucosylceramide of about 4.6 µg/ml or less. Below the 10$^{th}$ percentile of the normal mean range of glucosylceramide considered to constitute a glucosylceramide deficiency represents a plasma concentration of glucosylceramide of about 4.2 µg/ml or less.

A low or below-normal level glucosylceramide in a biological specimen, in particular, in plasma is a risk factor for an individual to have thrombosis. The type of thrombosis includes venous thrombosis such as occurs in stroke, surgery, trauma, cancer, leg paresis, prolonged travel, oral contraceptive use, estradiol use, hormone replacement therapy, during or following pregnancy, inflammatory bowel disease, Bechet's disease, bone fracture, hyperlipidemia, chemotherapy use, diabetes, or in subjects carrying a genetic risk factor for thrombophilia such as a protein S deficiency and the like. Such individuals will benefit from therapy using the antithrombotic neutral glycolipid of the present invention to enhance APC:Protein S anticoagulant activity for prevention or inhibition thrombosis.

Therapy using the antithrombotic neutral glycolipid of the present invention is useful for vascular disorders involving arterial or venous thrombosis including but not limited to:

1. Acute arterial thrombotic occlusion including coronary, cerebral or peripheral arteries, including myocardial infarction, reperfusion injury and stroke,
2. Acute thrombotic occluson or restenosis after angioplasty,
3. Reocclusion or restenosis after thrombolytic therapy, ischemic tissue when used within hours of acute heart attack or stroke by re-establishing blood flow in the occluded artery,
4. Small and large caliber vascular graft occlusion. Vascular grafts of small caliber, i.e., 3-/mm diameter, have a high frequency of thrombotic occlusion,
5. Hemodialysis. The prosthetic surfaces and flow design of all hemodialyzers are thrombogenic. Currently heparin is infused during dialysis. However, heparin is only partially effective, thereby limiting the reuse of dialyzers. Also, heparin has a number of troublesome side effects and complications,
6. Cardiopulmonary bypass surgery to prevent thrombus formation in the oxygenator and pump apparatus,
7. Left ventricular cardiac assist device. This prosthetic pump is highly thrombogenic and results in life threatening thromboembolic events—complications that are only partially reduced by convential anticoagulants (heparin or coumarin drugs).
8. Total artificial heart and left ventricular assist devices.
9. Other arterial thrombosis. Neutral glycolipids are useful for arterial thrombosis or thromboembolism where current therapeutic measures are either contraindicated or not effective. For example, neutral glycolipids are useful for the treatment of acute pre-or postcapillary occlusion, including transplantations, retina thrombosis, disseminated intravascular coagulation, arteritis of any cause, or microthrombotic necrosis of any organ complicating infections, such as sepsis, tumors or coumarin treatment.

Neutral glycolipid therapy may reduce the doses of t-PA or other thrombolytic agents required for therapeutic treatment of thrombosis, thereby avoiding the complications of high doses of thrombolytic agents.

The neutral glycolipids of the present invention are also useful in preventing, inhibiting or reducing inflammation in a subject having or at risk of having inflammatory vascular disease. The method includes administering to the subject, an anti-inflammatory effective amount of neutral glycolipid, for example, in a pharmaceutically acceptable carrier, thereby reducing inflammation in the subject.

The present invention is useful for treating many clinical conditions involving inflammatory processes. For example, inflammatory bowel diseases including Crohn's disease and ulcerative colitis are spontaneous chronic inflammations of the gastrointestinal tract which involve activation of inflammatory cells whose products cause tissue injury Neutrophils, eosinophils, mast cells, lymphocytes and macrophages contribute to the inflammatory response.

The present invention is also directed to treatment of systemic shock and many resultant clinical conditions associated therewith. Systemic shock often occurs as a complication of severe blood loss, severe localized bacterial infection and ischemia/reperfusion trauma and it is a major cause of death in intensive care units. Most cases of septic shock are induced by endotoxins (i.e. bacterial cell wall lipopolysaccharides or LPS) from gram negative bacilli or toxins (i.e. toxic shock toxin 1) from gram positive cocci bacteria. The release of LPS in the bloodstream causes release of inflammatory mediators (inflammatory cytokines, platelet activating factor, complement, leukotrienes, oxygen metabolites, and the like) which cause myocardial dysfunction, vasodilation, hypotension, endothelial injury, leukocyte adhesion and aggregation, disseminated intravascular coagulation, adult respiratory distress syndrome (ARDS), liver, kidney and central nervous system (CNS) failure. Shock due to blood loss also involves inflammatory mediator release. In each case, inflammatory responses are induced at the original site of trauma, and also in the vasculature and remote vascularized sites.

Myocardial ischemia is associated with activation of the complement system which further promotes cardiac injury with the enhancement of a series of inflammatory events. Life threatening local and remote tissue damage occurs during surgery, trauma and stroke when major vascular beds are deprived for a time of oxygenation (ischemia), then restored with normal circulation (reperfusion). Reperfusion injury is characterized by vascular premeability leading to edema and infiltration of inflammatory cells. Neutrophils contribute significantly in reperfusion damage by generating oxidants or releasing proteases that damage the microvasculature or adjacent tissue. Cell death and tissue damage due to complement and inflammatory cell mechanisms lead to organ failure or decreased organ function. The activation of mediators by a local injury can also cause a remote injury to highly vascularized organs. The compositions and methodologies of the present invention are useful in the treatment of ischemia and reperfusion injury.

Inflammatory response damage also occurs in glomerulonephritis as well as tubule disease. Infiltration of inflammatory cells (especially macrophages) is linked to proteinuria accompanied histologically by hypercellularity and crescent formation in glomeruli. Over a longer term, the infiltraton of inflammatory cells is associated with accumulation of extracellular matrix and sclerosis and chronic compromise of renal function. The present invention is also efficacious in treating glomerulonephritis and tubule disease.

There are many other diseases and injury conditions which benefit from the methodologies of the present invention such as for example, coronary arterial occluson, cardiac arrhythmias, congestive heart failure, cardiomyopathy, bronchitis, acute allergic reactions and hypersensitivity, neurotrauma, graft/transplant rejection, myocarditis, insulin dependent diabetes, Alzheimer's disease and stroke. Stroke involves a very strong inflammatory response, that in part may be responsible for neuronal damage directly by allowing leukocytes to enter the brain and destroy normal brain cells and neurons, and indirectly by obstructing microvessels and stopping blood flow. This requires adhesion molecules and cytokines that may be direct or indirect targets of neutral glycolipids that may be independent of its anticoagulant effects.

In addition to treating patients suffering from the trauma resulting from heart attack, patients suffering from actual physical trauma could be treated with neutral glycolipids to relieve the amount of inflammation and swelling which normally result after an area of the body is subjected to severe trauma. Also, patients suffering from hemorrhagic shock could be treated to alleviate inflammation associated with restoring blood flow. Other disease states which might be treatable using formulations of the invention include various types of arthritis, various chronic inflammatory conditions of the skin, insulin-dependent diabetes, and adult respiratory distress syndrome. After reading the present disclosure, those skilled in the art will recognize other disease states and/or symptoms which might be treated and/or mitigated by the administration of neutral glycolipids formulations of the present invention.

The present invention provides methods for screening candidate neutral glycolipids or mimetics for those useful in the prevention or treatment of a neutral glycolipid deficiency in an individual and for prevention, inhibition or treatment of thrombosis and inflammation. Any of the standard coagulation or clotting assays may be used to screen for anti-thrombotic factors from among candidate neutral glycolipids. Such assays include but are not limited to prothrombin clotting assays, Factor Va inactivation assays and the like. A generalized assay is disclosed in U.S. Pat. No. 5,443,960, incorporated herein by reference.

In one embodiment, A method of screening for antithrombotic factors from candidate neutral glycolipids comprising:
  (i) incubating the candidate neutral glycolipid with a plasma sample with:
    (1) exogenous activated protein C, exogenous protein C and an exogenous reagent that transforms exogenous protein C to activated protein C, or an exogenous reagent that transforms endogenous protein C to activated protein C;
    (2) an exogenous reagent (I) which at least partially activates a coagulation factor of the blood coagulation system of said plasma sample; and optionally;
    (3) an exogenous substrate for an enzyme wherein the activity of said enzyme is influenced by neutral glycolipid, to prepare a final assay medium;
  (ii) measuring a substrate conversion rate for a coagulation factor directly or indirectly activated in step (i), the activity of which is influenced by neutral glycolipid; and
  (iii) comparing said substrate conversion rate measure in step (ii) with a standard value obtained from plasma in the absence of said neutral glycolipid wherein when said substrate conversion rate obtained for said neutral glycolipid in step (ii) is lower than the standard value, said candidate neutral glycolipid is an antithrombotic factor.

The incubation according to (i:a) serves to introduce an activated coagulation factor that can be used for the measurement in step (ii). The expression "partially" means that the addition of Reagent (I) leads to the presence of at least Factor $IX_a$. Reagent (I) may be a certain coagulation factor or a reagent that activates the system via the intrinsic or extrinsic pathway. Accordingly Reagent (I) may be Factor $IX_a$ or Factor $XI_a$ (intrinsic pathway), Factor $XII_a$ (intrinsic pathway), kallikrein (intrinsic pathway) a contact activator (intrinsic pathway) such as kaolin, celite or ellagic acid (intrinsic pathway), an APTT reagent (Activated Partial Thromboplastin Time; i.e. a reagent containing a phospholipid and a contact activator (intrinsic pathway), tissue thromboplastin (PT-reagent, PT-Prothrombin time, (extrinsic pathway)). In cases here a poor specificity is acceptable Reagent (I) may also be Factor $X_a$.

Protein C (i:b) may be of various species origin. In case the protein C and the sample are of different species origin it is highly recommended to include protein S (cofactor to activated protein C) in the incubation mixture. Protein C and protein S should be of the same species origin, for instance bovine protein C requires bovine protein S. Protein C is preferably activated prior to being added, although activation may also be accomplished after it has been added to the sample. Activation shall take place under standardised and definied conditions. Recombinantly produced biologically functional forms of protein C and S can also be used.

The components used according to step i:c depend on the mode employed and may necessitate the inclusion of plasma protease inhibitors for enzymes other than the monitored one or of a fibrin polymerization inhibitor. $Ca^{2+}$ may be in the form of a plasma soluble salt that provides the $Ca^{2+}$ ion in free uncomplexed form, i.e. strong $Ca^{2+}$ chelators should be avoided. In the final assay medium the concentration of $Ca^{2+}$ may be selected within 0.5–50 mM, preferably within 5–15 mM, such as 6–7 mM. Too high a concentration may inhibit the coagulation system.

The substrate according to (i:d) is normally a synthetic substrate for an enzyme which activity is influenced by activated protein C, e.g. thrombin (=Factor $II_a$) and Factor $X_a$. Suitable synthetic substrates are water soluble and have preferably oligopeptide structure with three, four or five amino acid residues and an amino terminal that is protected from being attacked by amino peptidases. The protection is accomplished either by a protecting group or by having a D-amino acid in the amino terminal. In order to give a detectable response the carboxy terminal of a synthetic substrate is amidated with a group that specifically can be released and detected upon action of the relevant blood coagulation protease. The group to be released is selected among chromogenic, fluorogenic or chemiluminogenic groups and other analytically detectable groups. See further H. C. Hemker, "Handbook of synthetic substrates for the coagulation and fibrinolytic system", Martinus Nijhoff Publishers, 1983, and J. Fareed et al, "Synthetic peptide substrates in hemostatic testing" in CRC Critical Reviews in Clinical Laboratory Sciences, Vol. 19, Issue 2, 71–134 (1983). In case of samples other than plasma samples exogenous fibrinogen may be added as substrate.

The order of addition and the incubation vary with the mode of the invention. For instance in case Reagent (I) is an APTT reagent (i:a) and the substrate conversion to be monitored is fibrinogen to fibrin, reagent (I) is added to the sample and allowed to maximally activate Factor XI to Factor $XI_a$. Then $Ca^{2+}$ (i:c) is added and the time for clotting measured. Activated protein C according to step (i:b) is introduced either simultaneously with, prior to or after the activaton to Factor $XI_a$. A PT-assay is performed similarly with additional of tissue thromboplastin (instead of the APTT reagent) to the sample in an amount sufficient for activaton of Factor X to Factor $X_a$ or Factor IX to Factor $IX_a$. Thereafter activated protein C (i:b) is added and finally the clotting time is measured as in any APTT assay. In case a synthetic substrate is used it can be added at any stage before or at the start of the monitoring reaction. In order to run the monitoring reaction with high specificity, the above-mentioned inhibitors may be introduced at any suitable stage into the reaction medium. For instance it may be appropriate to add a thrombin inhibitor together with a substrate for Factor $X_a$, when Factor $X_a$ activity is measured. The same inhibitor added prior to addition of the substrate may, however, adversely affect the formation of Factor $X_a$.

In another embodiment, a method of screening for antithrombotic factors from among candidate neutral glycolipids comprising: A) adding vesicles containing a candidate neutral glycolipid to plasma in the presence of fibrinogen, activated protein C and protein S; B) measuring clotting time after addition of tissue factor and calcium ions, wherein prolongation of clotting time in comparison to a control is indicative of the neutral glycolipid as on antithrombotic factor.

In another embodiment, a method of screening for a antithrombotic factor from a candidate neutral glycolipid, comprising:

(1) incubating a candidate neutral glycolipid with a reaction mixture comprising activated protein C, protein S, Factor Va and a calcium source for a period sufficient for an enzymatic reaction with Factor Va;

(2) stopping the enzymatic reaction;

(3) determining the amount of Factor Va inactivation, wherein an increase in Factor Va inactivation by greater than 5 percent compared with control in the absence of the candidate neutral glycolipid indicates the neutral glycolipid is an antithrombotic factor.

The present invention also provides an animal model for thrombosis comprising an animal deficient in glucosylceramide. The deficiency may be induced by administration of an inhibitor of glucosylceramide synthase. Alternatively, the glucosylceramide deficiency is induced by genetic alteration of genes that regulate glucosylceramide synthesis, transport, processing, metabolism or hydrolysis. Such animal models are useful in screening for antithrombotic factors from candidate neutral glycolipids or mimetics useful for prevention or treatment of thrombosis and for correction of glucosylceramide deficiencies.

All the essential materials and reagents required for determining neutral glycolipid levels in a sample, for inhibiting thrombosis or inflammation or for screening for thrombolytic factors may be assembled together in a kit. When the components of the kit are provided in one or more liquid solutions, the liquid solution preferably is an aqueous solution, with a sterile aqueous solution being particularly preferred.

For the detection of neutral glycolipids the kit may contain materials for chromatographic separation, such as columns, beads, resins, gel matrices, filters, TLC plate, buffers and appropriate solvents. Alternatively, if the deteciton is via immunologic means, the kit may contain antibodies directed to the neutral glycolipid, secondary antibodies that binding primary antibodies, labels or signal generating compounds (either conjugated or unconjugated) and various reagents for the generation and detection of signals.

For screening for thrombolytic factors from candidate neutral glycolipids the kit may contain one or more reagents for conducting a clotting assay or Factor Va inactivation assay such as activated protein C, protein S, $CaCl_2$, Factor V, plasma, fibrinogen, EDTA, neutral glycolipid standards and the like.

For in vivo use, an antithrombotic neutral glycolipid, alone or in combination with an anticoagulant, antithrombotic, thrombolytic agent, antiplatelet drug, anti-inflammatory drug, high density lipoprotein or portion thereof, and combinations thereof, agent may be formulated into a single or separate pharmaceutically acceptable syringeable compositon. In this case, the container means may itself be an inhalent, syringe, pipette, eye dropper, or other such like apparatus, from which the formulation may be applied to an infected area of the body, such as the lungs, injected into an animal, or even applied to and mixed with the other components of the kit.

The components of these kits may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the antithrombotic or anti-inflammatory neutral glycolipid and/or other active ingredients or explaining the assays for determining neutral glycolipid levels in samples.

The kits of the present invention also will typically include a means for containing the vials in close confinement for commercial sale such as e.g., injection or blow-molded plastic containers into which the desired vials are retained. Irrespective of the number of type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle. Other instrumentation includes devices that permit the reading or monitoring of reactions in vitro.

The following example are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without department from the spirit and scope of the invention

EXAMPLE 1

Materials and Methods

Patient and control groups. The study population consisted of 70 Caucasian venous thromboembolism (VTE) cases and 70 Caucasian controls (50 of each from the University of Vienna and 20 of each from the Mayo Clinic), and all subjects gave informed consent. The baseline characteristics for patients from the two medical centers were similar. Patients from the two centers had a similar prevalence of features typical of venous thrombophilic patients, including 20–26% prevalence of Q506-factor V and 10–15% prothrombin 20210A. For all patients, the diagnosis of VTE was confirmed by objective methods (phlebography, compression duplex ultrasonography, pulmonary computerized tomography or perfusion-ventilation lung scan). The site of the first diagnosed VTE was deep leg vein thrombosis (DVT) in 40, DVT and pulmonary embolism in 14, pulmonary embolism without evidence of DVT in 11, deep arm vein thrombosis in 3, and cerebral vein thrombosis in 2 patients, respectively. Blood samples were collected at least three months after an episode of thrombosis. The first VTE event occurred spontaneously in 43 of 70 patients (61%). These "spontaneous" cases included 4 women receiving oral contraceptives, one woman with previous breast cancer, and one man with previously resected prostate cancer at the time of thrombosis. At the time of blood sampling (but not at the time of thrombosis) 2 women each were taking oral contraceptives or hormone replacement therapy, and one was taking tamoxifen. Because several Mayo Clinic patients were receiving anticoagulant therapy or had evidence of antiphospholipid antibody syndrome at the time of blood sample collection, we report coagulation studies only for Vienna patients without lupus anticoagulant and controls (n=50 each).

Seventy healthy individuals (41 women, 29 men) without a history of venous or arterial thromboembolism with a mean age of 42±14 years old (range 19–85) served as a control group. These healthy laboratory blood donors were routine volunteers who were not taking oral contraceptives or estrogen replacement therapy. For an additional determination of normal GlcCer levels, a panel of 40 normal adult donors (20 male, 20 female) was collected at The Scripps Research Institute (35.8±7.1 years old, range 19–56). Normal subjects gave informed consent for studies approved by appropriate institutional review. Blood samples were obtained from routine venipuncture after an overnight fast, then mixed with 0.129 M sodium citrate (plasma:citrate 9:1 (vol/vol)). Plasma was prepared by centrifugation at 2,000× g for 20 min at room temperature and then stored at −80° C. prior to analysis.

TABLE 1

Deep Vein Thrombosis Patient Characteristics

| Characteristic | | |
|---|---|---|
| Total | | |
| n = 70 | | |
| Current Age, (Mean ± SD), years | | |
| Range | 50.1 ± 14.4 | |
| (21–79) | | |
| Mean Age at first VTE episode, years | 45.5 ± 14.2 | |
| Gender (female), n (%) | 35 | (50) |
| Recurrent VTE, n (%) | 18 | (26) |
| Spontaneous VTE, n (%) | 43 | (61.4) |
| Recent surgery, n (%) | 4 | (5.7) |
| Recent trauma, n (%) | 8 | (16) |
| Active malignant neoplasm, n (%) | 3 | (4.3) |
| Previous malignant neoplasm, n (%) | 2 | (2.8) |
| Leg paresis, n (%) | 1 | (1.4) |
| Prolonged travel, n (%) | 4 | (5.7) |
| Oral contraceptive, n (%) | 4 | (5.7) |
| Other, n (%) | | |
| Puerperium | 1 | (1.4) |
| Inflammatory bowel disease | 2 | (2.9) |
| Bechet's disease | 1 | (1.4) |
| Tamoxifen use | 1 | (1.4) |

Lipid analysis. Plasma lipids were extracted twice from citrated plasma with four volumes of chloroform-methanol (2:1, v/v) (25). A Waters high performance liquid chromatography (HPLC) system (Waters Corp., Milford, Mass.) coupled to a Sedex-55 evaporative light scattering detector system (ELSD) (SEDERE, Vitry sur Seine, France) was used for GlcCer analysis as previously described for quantitation of cardiolipin in plasma, unless otherwise noted (25). A μPorosil column (300 mm×3.9 mm) was used with isocratic chloroform/methanol/0.5% trifluoroacetic acid/water (79:19:1:1). Under this condition, purified reference GlcCer (human spleen, Sigma, St Louis, Mo.) showed one peak eluting at 4.1 min (data not shown). The identity of the putative GlcCer peak observed for plasma extracts on the μPorosil column was confirmed based on having the same retention time at 4.1 min as reference GlcCer and on observing the predicted increase in peak area when purified GlcCer was added to plasma lipid extracts prior to HPLC analysis. Furthermore, the plasma-derived lipid obtained from the HPLC peak eluting at 4.1 min comigrated with reference GlcCer on thin layer chromatography (TLC) when using either chloroform/methanol/hexane/acetic acid 50:10:30:5 (v/v), chloroform/methanol/ammonium hydroxide 65:25:4 (v/v), or chloroform/methanol/water 60:30:5 (v/v) as developing solvents, respectively.

Material from the GlcCer HPLC peak eluting at 4.1 min showed one spot on TLC corresponding to purified GlcCer, and the spot, as well as reference GlcCer were stained by the α-napthol sugar test (26). When the following lipids were applied to this p-Porosil HPLC column, the GlcCer peak at 4.1 minutes was separated from peaks for all these lipids: other plasma glycolipids such as lactosylceramide (LacCer) (Matreya, Inc., Pleasant Gap, Pa.), globotriaosylceramide (Gb3Cer) and globotetraosylceramide (Gb4Cer) (Sigma); phospholipids, such as phosphatidylcholine (PC), lysophosphatidylcholine, PE, sphingomyelin, phosphatidylserine (PS) and phosphatidylinositol, cardiolipin, phosphatidylglycerol, and phosphatidic acid; cholesterol; or free fatty acids. To quantify GlcCer, a calibration curve was made by analyzing varying amounts of reference GlcCer (Sigma) using HPLC as previously described for standardization of cardiolipin (25) and the standard curve was fitted by the equation, Area=$2.37\times10^{6}\times[GlcCer (\mu g)]^{1.73}$, covering the range 0.1 to 2.0 μg GlcCer (data not shown).

Digestion of plasma GlcCer by glucocerebrosidase. Endogenous plasma GlcCer was hydrolyzed by two different glucocerebrosidases (β-glucosidase) (Sigma, St. Louis, Mo.), recombinant glucocerebrosidase (1.35 U/mg specific activity) or almond-derived glucocerebrosidase (2.85 U/mg specific activity) which are relatively specific hydrolases for GlcCer. Plasma was incubated with varying concentrations of glucocerebrosidase for 3 min, and then lipid was extracted from plasma aliquots using chloroform/methanol for GlcCer determination using HPLC. In these studies determining hydrolysis of GlcCer by glucocerebrosidase, the concentration of PE, which was not hydrolyzed by glucocerebrosidase, was used as internal standard for lipid recovery. In parallel, prothrombin time assays (see below) were performed using aliquots of glucocerebrosidase-treated plasma.

Anticoagulant response to APC:protein S. Modified dilute prothrombin time based assays were performed as previously described. Briefly, 7.5 μl of test plasma was mixed with fibrinogen (0.6 mg/ml final concentration) and APC (8.7 nM final) plus protein S (28 nM final) or buffer, and incubated 3 min at 37° C. (100 μl total volume). Clotting times were measured after addition of 50 μl of recombinant human tissue factor (Innovin from DADE, Miami, Fla.) diluted 1:40 in Tris (tris[hydroxymethyl] aminomethane)-buffered saline containing 0.5% bovine serum albumin (TBSA) and 30 mM $CaCl_2$. Baseline clotting times without addition of APC:protein S were also determined. For studies of the effects of glycolipid vesicles or glucocerebrosidase treatment on clotting assays, a 1:64 dilution of Innovin was used in the presence or absence of APC and protein S. In the study of the effect of glucocerebrosidase, 13 nM APC and 42 nM protein S were employed.

Preparation of glycolipid vesicles. To prepare extruded glycolipid vesicles, dried glycolipids GlcCer, Gb3Cer, galactosylceramide (GalCer) (Sigma), and LacCer were suspended at 100 μg/ml in TBS at room temperature, vortexed 5 min, and passed through a 0.2 μm filter (Osmonics, Livermore, Calif.). Concentrations of glycolipids recovered after filtration were determined by HPLC analysis as described above.

Large unilamellar multicomponent vesicles were prepared generally as described. (27) Appropriate aliquots of PC, PS and GlcCer were mixed and dried under nitrogen. The lipid mixture was hydrated at a concentration of 6.25 mM lipid in TBS and freeze-thawed 10 times using liquid nitrogen, and the solution of vesicles was passed 15 times through a 0.2 μm filter (Millipore). Concentrations of glycolipid recovered after filtration were determined by HPLC analysis as described above. PC concentration was determined by an enzymatic calorimetric method (Phospholipids B kit, Wako Chemical USA, Inc., Richmond, Va.).

Factor Va inactivation assay. To study the time course of factor Va inactivation by APC:protein S, mixtures containing GlcCer vesicles or control PC vesicles (21.5 μM) or buffer, APC (6 nM final), protein S (18 nM final), and factor Va (1.5 nM) with 5 mM $CaCl_2$ were incubated at 37° C. Aliquots were withdrawn at various times and the reaction was quenched by adding ethylenediamine tetraacetic acid (EDTA) prior to determination of residual factor Va activity. For the various lipid mixtures (PC alone, PC/GlcCer (90%/10%, weight/weight), PC/PS (90%/10%) and PC/PS/GlcCer (80%/10%/10%)), vesicles at varying concentrations were incubated with APC (1 nM final), protein S (18 nM final), and factor Va (1.5 nM final) for 3 min at 37° C., and then the reaction was quenched by adding EDTA. The residual factor Va activity was quantitated using prothrombin time clotting assays and standard log-log calibration curves of clotting time versus factor Va concentration generated using purified factor Va and factor V deficient plasma. (21)

Statistical analysis. Statistical analyses were performed by using PrismTM 3.0 software (Graph Pad Software, Inc., San Diego, Calif.) to determine correlations using the two-tailed Pearson test with 95% confidence interval. Mean and SD values for various plasma lipid levels were derived from distributions based on logarithm-transformation of observed values. Statistical significance between two groups was determined using the Students t-test (unpaired, two-tailed with 95% Cl) (Prism 3.0) and the difference was considered significant when $p \leq 0.05$.

EXAMPLE 2

Plasma GlcCer and PE in Patients with Deep Vein Thrombosis

A method to quantitate both GlcCer and PE in plasma extracts using HPLC was developed and validated as described in Materials and Methods. When GlcCer and PE in fasting plasma lipid extracts from 70 patients with deep vein thrombosis and 70 controls were quantitated and logarithm-transformed data were analyzed, the mean±SD plasma GlcCer level in patients was 4.89 µg/ml (3.1–7.4) compared with 6.54 µg/ml (4.4–9.7) in controls (FIG. 1A), and the difference was statistically significantly (p=0.0007). As a measure of relative risk, the odds ratio for deep vein thrombosis in subjects with GlcCer levels below the $10^{th}$ percentile of controls was 5.7 (95% Cl 2.3–14).

Figure 1B:
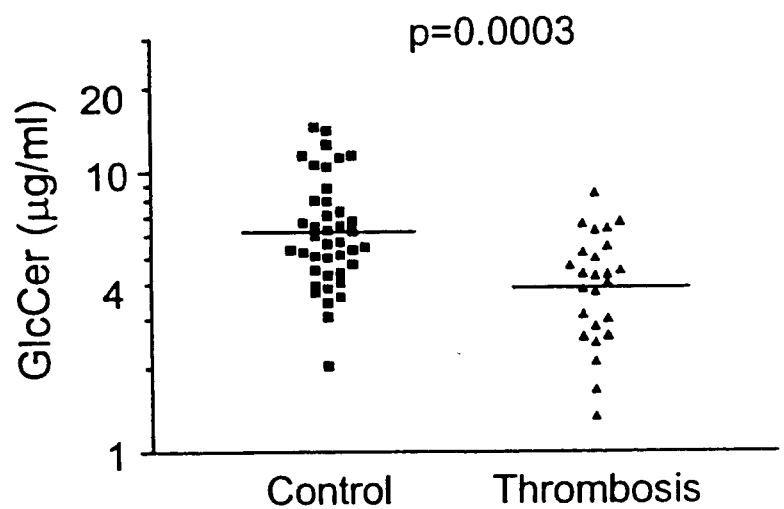
Figure 1C:
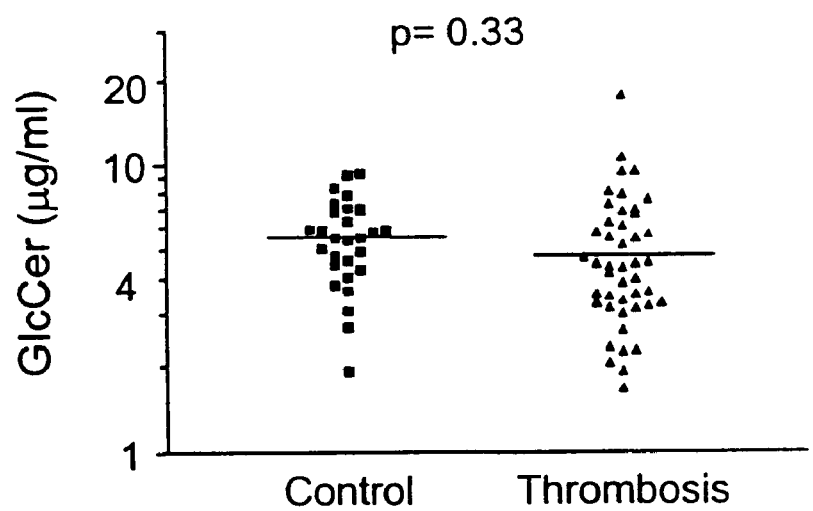
Figure 1D:
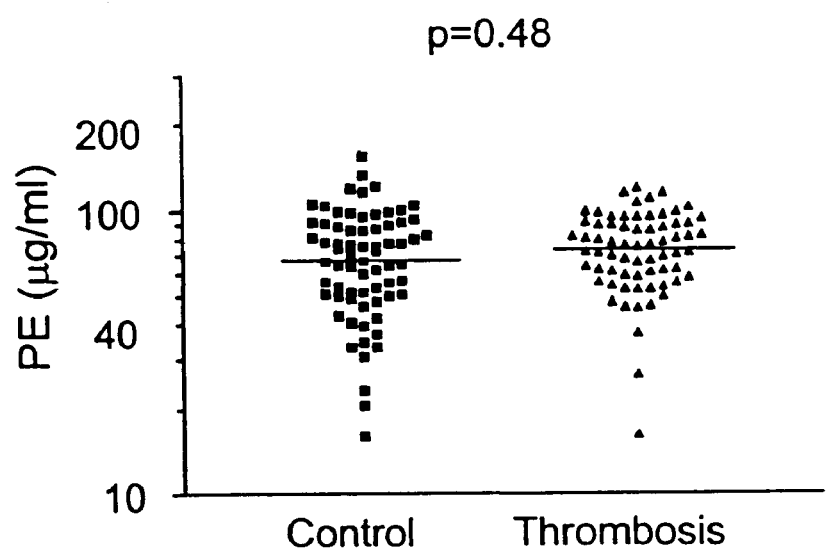

In contrast to GlcCer, no significant difference between patients and controls was seen for mean (±SD) plasma PE levels (p=0.48) that were 70.6 (50–100) µg/ml and 65.45 (42–102) µg/ml, respectively (FIG. 1D). As previously determined (25), for another normal control panel of 40 blood donors (The Scripps Research Institute subjects) the mean level of GlcCer was 6.9 µg/ml (range of observed values 4.2–14.7 µg/ml) and the mean level of PE was 66 µg/ml (range of observed values 16.1–156 µg/ml). These values did not differ significantly from those of the 70 controls (FIGS. 1A and 1D) from the University of Vienna and the Mayo Clinic (p=0.71 and p=0.31, respectively). Moreover, the mean plasma GlcCer value reported here for each control group is comparable to previously reported normal values, thus validating our quantification of plasma GlcCer. The influence of gender on plasma GlcCer levels was analyzed. There were no statistically significant differences between mean values of plasma GlcCer for male or female controls (p=0.54) or for male and female patients (p=0.67) (data not shown), thereby showing no influence of sex on plasma GlcCer levels. A slight influence of age on plasma GlcCer level was noted for the entire group of 140 subjects ($r^2$=0.043, p=0.014) and for the 70 controls ($r^2$=0.062, p=0.038) but not for the 70 patients (p=0.78) (data not shown). This small influence of age was insufficient to alter the statistically significant differences between patients and controls.

Patients were separated into those experiencing thrombosis at less than 44 years old and those who were at least 45 years old. When each group of patients was compared with the corresponding controls, the mean low GlcCer level were significantly lower for younger thrombosis patients (4.4 µg/ml) compared with controls (6.9 µg/ml) (FIG. 1B) (p=0.0003) but not for older thrombosis patients (5.2 µg/ml) compared with controls (6.1 µg/ml) (FIG. 1C) (p=0.33). When patients and controls who were at least 45 years old were analyzed, the odds ratio for deep vein thrombosis for GlcCer levels below the $10^{th}$ percentile value of controls was 5.2 (95% Cl of 1.4 to 19.4). This odds ratio of 5.2 was similar to that of 5.7 for the overall group of 70 thrombosis patients compared with 70 controls.

For the groups aged less than 44 years old, the mean ages of patients and controls at the time of plasma sampling were 34.4 and 32.4 years old, respectively, and were not significantly different (p=0.25). Comparison of the GlcCer values for patients with the $10^{th}$ percentile value of controls who were 45 years old gave an odds ratio for venous thrombosis of 1.87 (95% Cl of 0.45 to 7.7) (p=0.33) (FIG. 1C). Although statistical significance for a difference in GlcCer between the older patients and controls was lacking, it may be noteworthy that 17% of patients (7 of 45) had low GlcCer values of 3.3 µg/ml compared with 6% of controls (2 of 29), suggesting that plasma GlcCer deficiency also occurs in older venous thrombosis patients. For each of the two age groups above or below 45 years old, mean PE values were not statistically significantly different between venous thrombosis patients and controls (p=0.57 and 0.15, respectively) (data not shown).

EXAMPLE 3

Figure 2:
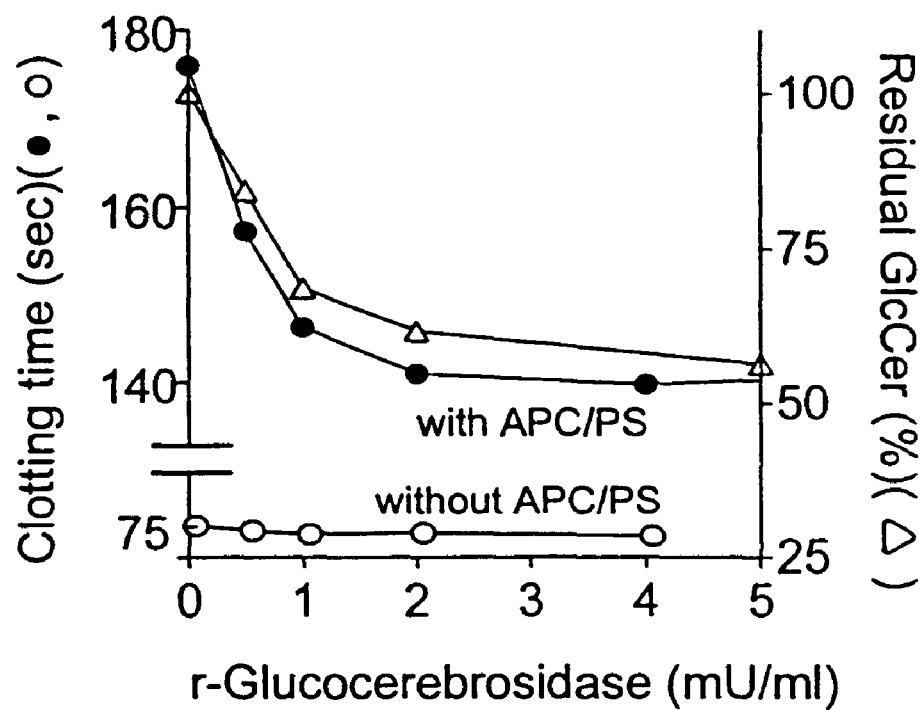
FIG. 2. Reduction of endogenous plasma GlcCer by recombinant glucocerebrosidase is associated with reduced anticoagulant response to APC:protein S. Following hydrolysis of endogenous plasma GlcCer for 3 min due to addition of recombinant glucocerebrosidase to plasma, the anticoagulant response to APC:protein S was immediately assayed and, using parallel aliquots, residual plasma GlcCer levels (right ordinate, Δ) were determined by HPLC analysis as described in Methods. The clotting times (left ordinate) observed in the presence (*) and absence (○) of APC:protein S are shown. The plasma GlcCer level prior to glucocerebrosidase treatment was defined as 100%.

Glucocerebrosidase Effect on Blood Coagulation and Anticoagulant Response to APC:Protein S To assess the direct influence of GlcCer in plasma on procoagulant reactions and on anticoagulant activities of APC:protein S, endogenous GlcCer in plasma was hydrolyzed by varying amounts of recombinant glucocerebrosidase. In parallel, glucocerebrosidase-treated plasma was analyzed for its coagulation properties and for loss of GlcCer. Recombinant glucocerebrosidase decreased the concentration of plasma GlcCer by approximately 50% in a dose-dependent fashion (FIG. 2). The anticoagulant response to APC:protein S, as reflected by shortening of observed clotting times (FIG. 2), was reduced in parallel to reduction of endogenous GlcCer concentrations. Similar results showing parallel decrease of plasma GlcCer and decreased response to APC:protein S were obtained in similar experiments using purified almond-derived glucocerebrosidase added to plasma (data not shown), proving that this effect was independent of the source of glucocerebrosidase. PE levels were not affected by this enzyme (±10%), showing that no significant phospholipid hydrolysis had occurred. Interestingly, in the absence of APC:protein S, recombinant glucocerebrosidase did not affect the baseline clotting times (FIG. 2). Thus, depletion of endogenous GlcCer by specific hydrolytic enzymes is associated with decreased anticoagulant response to APC:protein S.

EXAMPLE 4

Influence of Exogenous Glycolipids on Anticoagulant Response of Plasma to APC:Protein S Several purified glycolipids including GlcCer, LacCer, Gb3Cer and GalCer in vesicles were added to plasma that was then assayed as described. (21) When GlcCer was added to plasma in the presence of APC:protein S, it caused dose-dependent marked prolongation of the modified PT assay (FIG. 3). Similar effects of GlcCer causing clotting time prolongation in the presence but not absence of APC:protein S were observed in factor Xa-1-stage assays performed without addition of exogenous lipids (data not shown). When APC alone was added without protein S, addition of GlcCer caused much less clotting time prolongation compared with APC plus protein S (FIG. 3). When protein S alone was added in the absence of APC, GlcCer had no effect on clotting times (data not shown). Gb3Cer, a trisaccharide-containing glycolipid in which the Glc unit of GlcCer is extended by two Gal units, had activity very similar to GlcCer (FIG. 3). However, GalCer which simply has Gal in place of Glc did not enhance APC:protein S action and had no effect on baseline clotting times (FIG. 3). Neither D-Glc alone nor ceramide alone (0–100 mg/ml) affected APC:protein S anticoagulant response (data not shown). Thus, the anticoagulant enhancement of APC's action by neutral glycolipids was stereospecific for the saccharide moieties.

EXAMPLE 5

Correlation of Anticoagulant Response to APC:Protein S with Plasma GlcCer Levels To assess the correlation between plasma GlcCer levels and procoagulant reactions or anticoagulant response, clotting assays using diluted tissue factor were performed (21) in the presence and absence of APC and protein S. For this analysis, plasmas from subjects known to carry Q506-factor V were excluded because of the significant influence of this polymorphism on anticoagulant response to APC. The anticoagulant response, as reflected by the clotting time in the presence of APC:protein S, was correlated with GlcCer levels for thrombosis patients (p=0.0035, r=0.45, n=37)

Figure 4A:
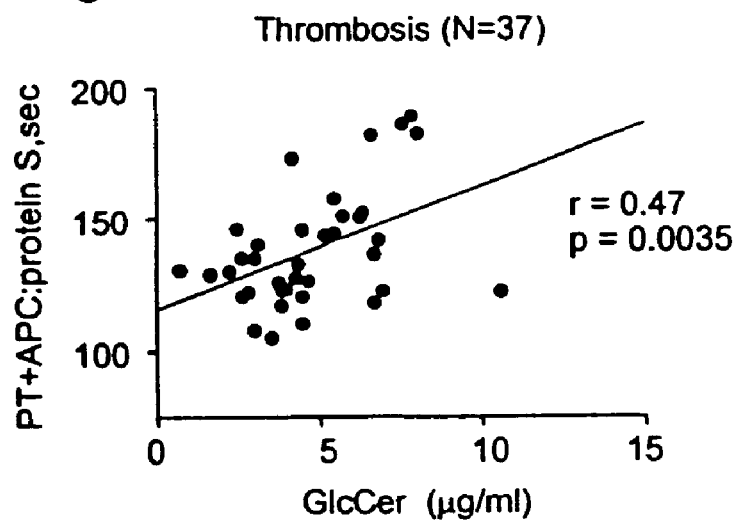
FIGS. 4A–4D. Correlation of anticoagulant response to APC:protein S with plasma GlcCer levels in venous thrombosis patients. Fasting plasma samples from 50 venous thrombosis patients and 50 controls were assayed using modified prothrombin time (PT) clotting assays in the presence and absence of added APC:protein S. Baseline PT values were determined in the absence of added APC:protein S. Parameters from analysis of the correlation between the observed clotting times and GlcCer are shown for each subgroup.
Figure 4B:
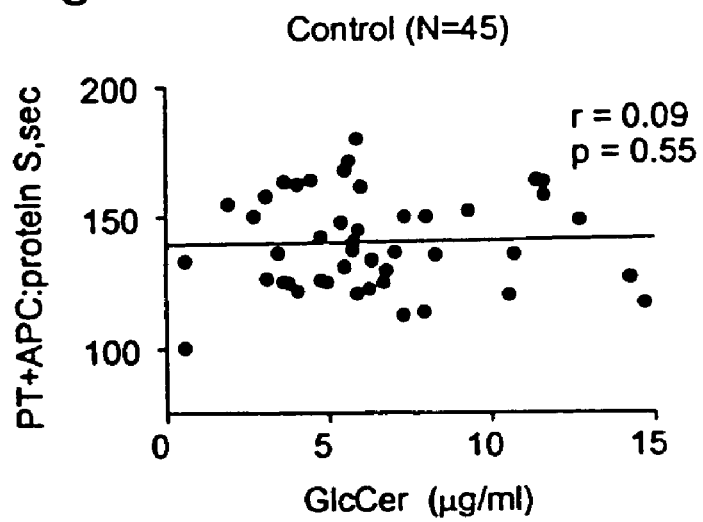
Figure 4C:
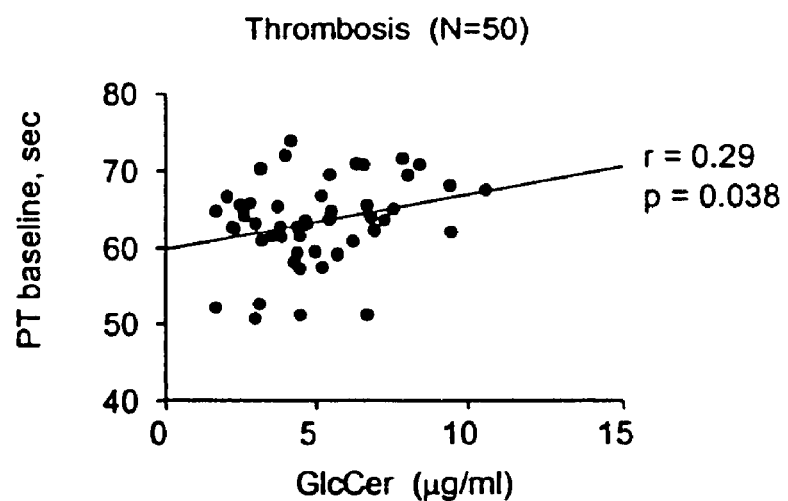
Figure 4D:
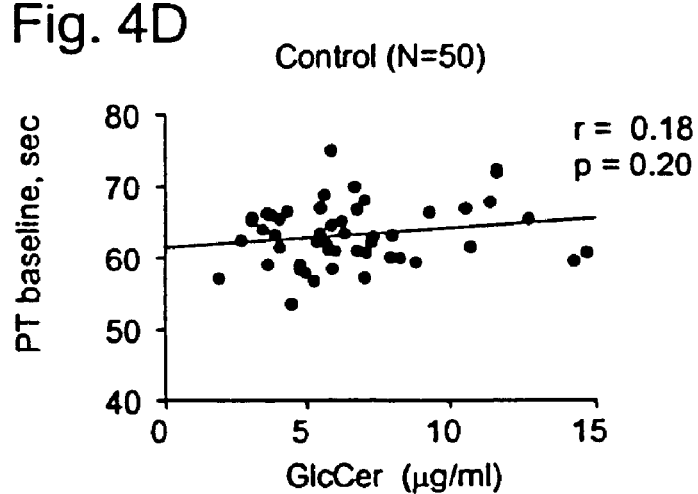

(FIG. 4A) but not for controls (p=0.55, n=45) (FIG. 4B). Further analysis of subgroups showed that this anticoagulant response correlated with GlcCer for male thrombosis patients (p=0.0025, r=0.65, n=19) but not for female thrombosis patients (p=0.21, r=0.31, n=18) (data not shown). Analysis of correlation between baseline clotting times for thrombosis patients (P=0.038, r=0.29, n=50) (FIG. 4C) and controls (P=0.18, r=0.20, n=50) (FIG. 4D).

EXAMPLE 6

Direct Effect of GlcCer on Purified Factor Va Inactivation

Figure 5A:
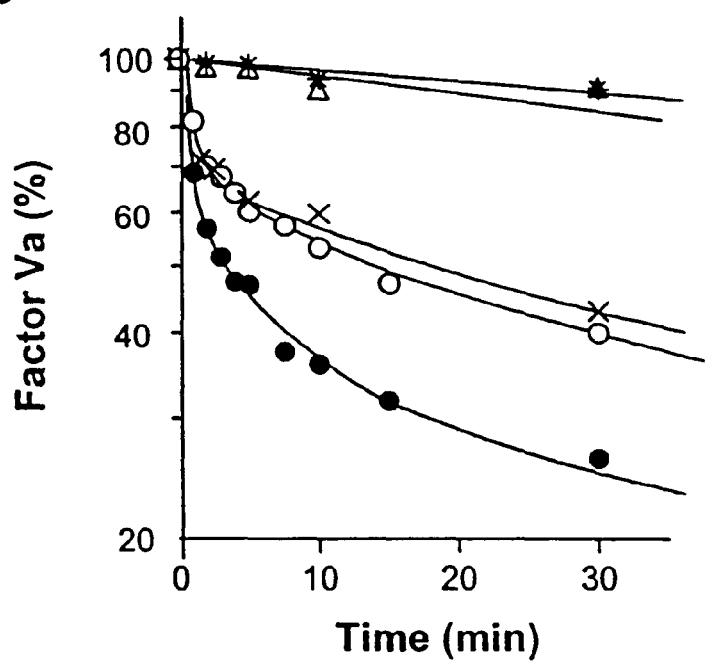
FIGS. 5A and 5B. GlcCer enhances factor Va inactivation by APC:protein S. Purified factor Va was incubated with APC:protein S and varying lipids to allow factor Va inactivation for times indicated, and then residual factor Va activity was determined using clotting assays as described in Materials and Methods.
Figure 5B:
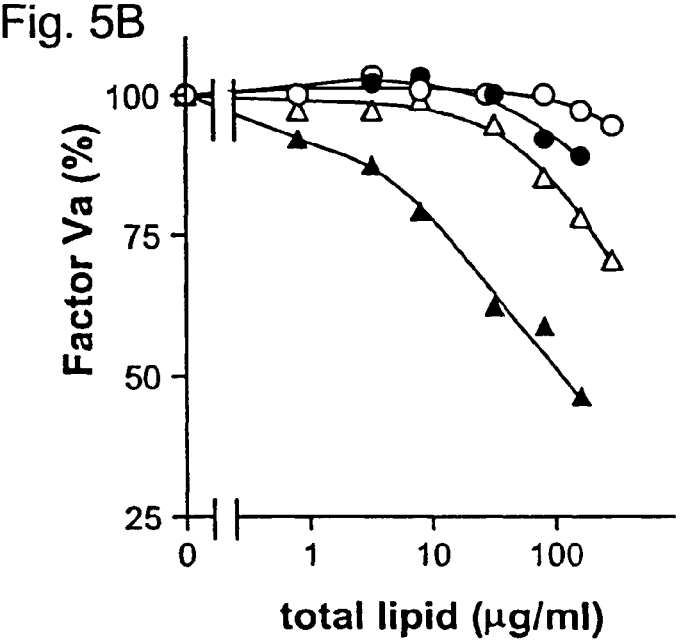

To test whether GlcCer vesicles have a direct effect on factor Va inactivation by APC:protein S in purified system, purified proteins were used to study the time course of factor Va inactivation. Factor Va inactivation by APC:protein S was enhanced by GlcCer vesicles compared with PC vesicles or buffer alone (FIG. 5A), indicating that GlcCer vesicles can directly enhance factor Va inactivation. Experiments were also performed to characterize the anticoagulant cofactor potency of GlcCer incorporated into multicomponent phospholipid vesicles. When such vesicles containing 10% GlcCer were used to stimulate inactivation of purified factor Va by APC:protein S, PC/GlcCer vesicles were more active than PC vesicles but less active than PC/PS vesicles (FIG. 5B). Incorporation of 10% GlcCer into PC/PS (80%/10%) vesicles enhanced factor Va inactivation compared with PC/PS (90%/10%) vesicles (FIG. 5B). The apparent potency of these tricomponent GlcCer/PC/PS vesicles was approximately an order of magnitude greater than PC/PS vesicles (FIG. 5B). Thus, GlcCer, can significantly directly enhance inactivation of purified factor Va by APC:protein S.

EXAMPLE 7

Direct Effect of Various Neutral Glycolipids on Purified Factor Va Inactivation Purified factor Va (1.5 nM) was incubated with APC (0.16 nM final)/protein S (18 nM final) and varying lipids vesicles to allow factor Va inactivation for 5 min., and then the residual factor Va activity was determined using prothrombin time clotting assays.

Figure 6A:
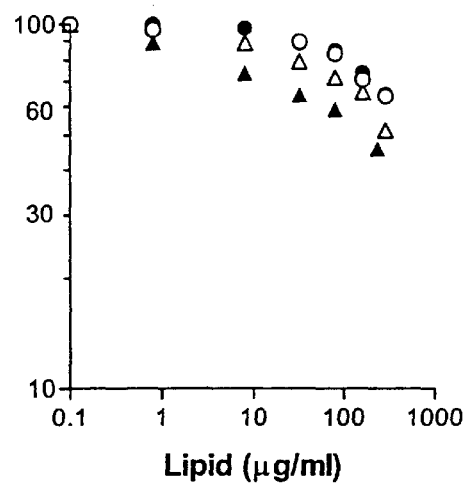
FIGS. 6A–6E. Anticoagulant response of plasma to APC/protein S is enhanced by addition of glycolipids. Purified factor Va (1.5 nM) was incubated with APC (0.16 nM final)/protein S (18 nM final) and varying lipid vesicles to allow factor Va inactivation for five minutes and then the residual factor Va activity was determined using prothrombin time clotting assays.
Figure 6B:
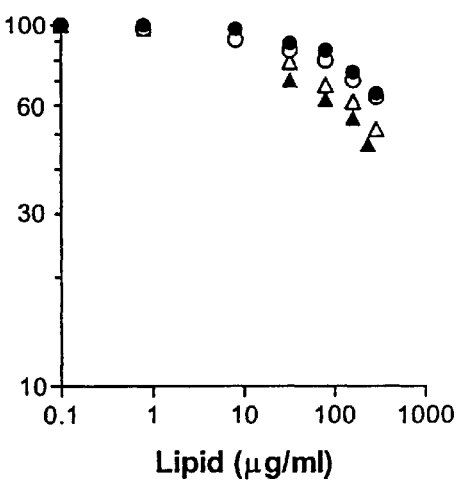
Figure 6C:
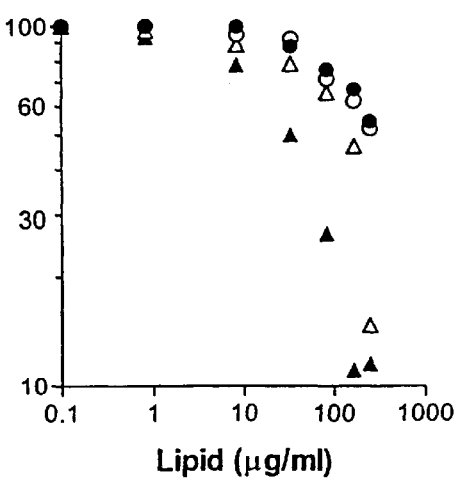
Figure 6D:
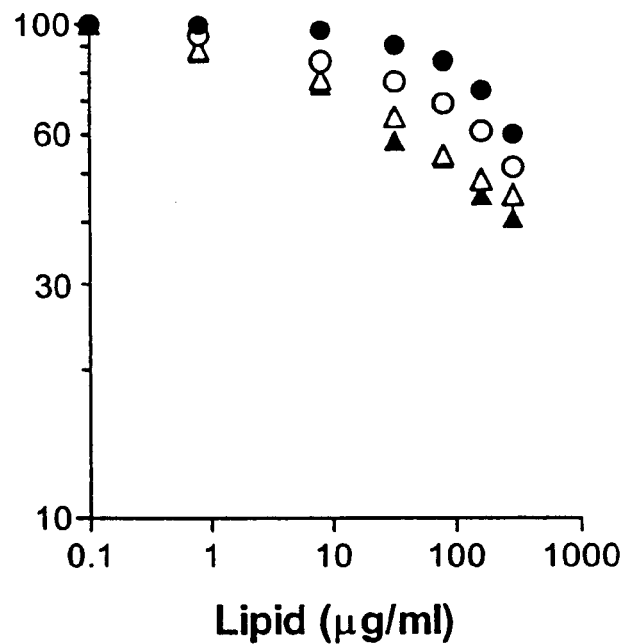
Figure 6E:
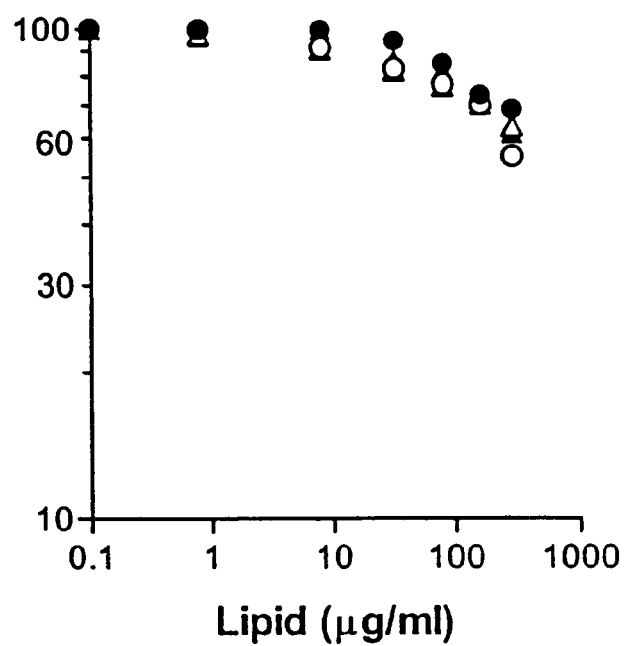

When various concentration of GlcCer in PC/PS vesicles were added to factor Va inactivation system, 1% GlcCer in PC/PS vesicle showed little enhancement effect of APC/protein S with PC/PS alone vesicle. 5 and 10% GlcCer in PC/PS vesicle enhanced inactivation of factor Va much more and reached up to 60% factor Va inactivation and this enhancement effect was observed from 1 $\mu$g/ml (FIG. 6A). The apparent potency of 10% GlcCer/PC/PS vesicles was approximately an order of magnitude greater than PC/PS vesicles. Thus, GlcCer can significantly directly enhance inactivation of purified factor Va by APC:protein S. Surprisingly, even 1% Gb3Cer containing vesicle already enhanced inactivation of factor Va significantly even at 1 $\mu$g/ml Gb3Cer in PC/PS vesicle, and 5% Gb3Cer in PC/PS enhanced much more but 10% Gb3Cer in PC/PS effect was similar to 5% Gb3Cer in PC/PS (FIG. 6C). One % of LacCer affect factor Va inactivation by APC/protein S little like GlcCer, and the effect of 5% LacCer were also similar to 5% GlcCer except for highest concentration. However, 10% LacCer dramatically enhanced factor Va inactivation and its inactivation was reached up to 90% under this condition (FIG. 6B). When GalCer in PC/PS were applied to factor Va inactivation assay, the effect of GalCer in PC/PS was not as well as GlcCer in PC/PS below 10 $\mu$g/ml where GlcCer in PC/PS vesicle already showed significant enhancment effect on factor Va inactivation by APC/protein S. Above 10 $\mu$g/ml of total lipid of GalCer in PC/PS, 5 and 10% GalCer containing vesicle enhanced factor Va inactivation by APC/protein C like GlcCer in PC/PS vesicle (FIG. 6E). Gb4Cer in PC/PS vesicle showed much weaker effect on factor Va inactivation (FIG. 6D) than GlcCer.

Thus, GlcCer, lactosylceramide, galactosylceramide and globotriaosylceramide incorporated into vesicles, can significantly directly enhance inactivation of purified factor Va by APC:protein S.

Based on our interest in the influence of plasma lipids and lipoproteins on the antithrombotic protein C pathway, (18–21, 25) we established HPLC-based methods to quantitate various plasma phospholipids, including cardiolipin, PS and PE. (25) The HPLC methodology used for PE analysis also permitted quantitation of the neutral glycosphingolipid, GlcCer. When the influence of GlcCer on anticoagulant response to APC:protein S was studied, we found that depletion of endogenous GlcCer by addition of glucocerebrosidase to normal pooled plasma proportionately reduces sensitivity to APC:protein S (FIG. 2) while addition of exogenous GlcCer to normal plasma dose-dependently enhances the anticoagulant response without affecting baseline clotting time (FIG. 3). Thus, plasma GlcCer appeared to act like an anticoagulant cofactor for APC:protein S, leading us to hypothesize that GlcCer would influence anticoagulant activity by enhancing APC:protein S in vivo and that GlcCer deficiency may predispose to thrombosis.

To test the hypothesis that plasma GlcCer deficiency is a marker or risk factor for thrombosis, plasma GlcCer and PE mean levels for 70 patients with deep vein thrombosis were compared to those for 70 healthy controls. This comparison showed a remarkably lower mean level of GlcCer, but not of PE, in patients compared with controls (p=0.0007 and 0.48, respectively). Plasma GlcCer levels did not differ by gender in patients or in controls. As a measure of relative risk, the odds ratio for deep vein thrombosis in subjects with low plasma GlcCer levels below the $10^{th}$ percentile of controls was 5.7 (95% Cl 2.3–14). For those under age 45 in whom hereditary risk factors might play a more easily identifiable role, the difference between plasma GlcCer values for patients and controls was remarkable (p=0.0003), and the odds ratio for venous thrombosis for subjects with GlcCer below the $10^{th}$ percentile of controls was 5.2 (95% Cl 1.40–19.4). These observations suggest that plasma GlcCer deficiency may be a marker or a risk factor for venous thrombosis and that younger age may be an important factor for low plasma GlcCer associated with venous thrombosis.

In suggesting that low plasma GlcCer could be a potential risk factor, rather than simply a marker, for venous thrombosis, we note that experiments here demonstrate biological plausibility for the ability of GlcCer to directly enhance the anticoagulant action of APC:protein S in both the plasma milieu and in reaction mixtures containing purified clotting factors. In normal plasma, depletion of endogenous GlcCer by enzymatic treatment decreased proportionately GlcCer levels and anticoagulant response to APC:protein S and, furthermore, when purified GlcCer was added to plasma, it dose-dependently enhanced this anticoagulant response. In studies using purified proteins, GlcCer directly enhanced inactivation of purified factor Va by APC:protein S. The direct anticoagulant effects of GlcCer were apparent for vesicles containing GlcCer in the absence and in the presence of PS.

The ability of glycolipids to enhance APC:protein S anticoagulant activity in plasma demonstrated specificity for the conformation and composition of the saccharide moieties. Anticoagulant activity appeared to be, at least in part, specific for D-Glc linked covalently to Cer because neither D-Glc alone nor ceramide alone was anticoagulantly active while GlcCer was very active and because GalCer was also inactive. The effects of extending the saccharide unit attached to Cer were complex because GlcCer (Glcβ1-Cer) and Gb3Cer (Galα1,4Galβ1,4Glcβ1-Cer) were approximately equally active whereas the disaccharide-containing glycolipid, LacCer (Galβ1,4Glcβ1-Cer), showed much lower activity than the highly active glycolipids containing either a monosaccharide or a trisaccharide.

The major plasma glycolipids which are associated with each major class of plasma lipoproteins, VLDL, LDL, and HDL, include GlcCer, LacCer, Gb3Cer and Gb4Cer with plasma levels of approximately 10, 5.5, 2.1, and 2.8 $\mu$M, respectively. (28) Their biological activities are partially determined by their sugar head groups and partially by their lipid moieties. LacCer accumulation in atherosclerotic lesions is caused by oxidized-LDL and is associated with atherosclerosis via stimulation of smooth muscle cell proliferation by superoxide generation. (29) Interestingly, in contrast to LacCer, neither GlcCer nor Gb3Cer supports this atherogenic reaction. (29) While not being bound by theory, we speculate that GlcCer and Gb3Cer could suppress thrombin generation which contributes to development of atherothrombosis by enhancing the APC:protein S anticoagulation system. Notably, LacCer does not possess this anticoagulant property. Thus, from these perspectives, LacCer may be considered an atherogenic glycolipid while GlcCer and Gb3Cer may be anti-atherothrombogenic glycolipids. Moreover, this specific activity of oxidized-LDL on selective accumulation of LacCer provides another case, in addition to that presented here, where a biologic activity of these three neutral glycolipids, each containing Glc linked to Cer by b1-linkage, is different for LacCer compared with GlcCer and Gb3Cer.

How does GlcCer directly enhance the anticoagulant action of APC:protein S? APC cleaves the heavy chain of factor Va at Arg506, and then Arg306, and perhaps Arg679, (30) and protein S and phospholipids are known to accelerate factor Va inactivation by selectively promoting the otherwise slow phospholipid-dependent cleavage at Arg306. (31) In purified protein systems, GlcCer might directly accelerate cleavage at Arg306, Arg506, or Arg679 in factor Va by APC in the presence of protein S by binding to one or more of these proteins. In the plasma milieu, there are additional potential mechanisms for GlcCer and its analogues. Protein S can abrogate the ability of factor Xa to protect factor Va from APC cleavage (32) and factor Va residues 493–506 provide binding sites for protein S and factor Xa, (33) it is also possible that GlcCer might enhance the ability of protein S to compete better with factor Xa for binding factor Va. Cleavage of factor V at Arg506 augments the anticoagulant cofactor activity of factor V for APC-dependent inactivation of factor VIIIa, and GlcCer might affect these anticoagulant reactions. (34) Moreover, it is possible that GlcCer associates with another plasma component that itself directly enhances APC:protein S anticoagulant activity, in which case the anticoagulant effect of GlcCer on APC:protein S would be an indirect one. Extensive studies are needed to define the mechanisms of action of GlcCer as an anticoagulant cofactor.

When data were analyzed for correlations between plasma GlcCer levels and anticoagulant response to APC:protein S, several patterns were observed (FIG. 4). For all venous thrombosis patients with normal factor V genotype, i.e., those who did not carry the APC-resistant Gln506-factor V, the anticoagulant response to APC:protein S correlated with GlcCer levels. However, analysis of patient subgroups showed that this correlation was significant only for males, and there was no statistically significant correlation for controls. The variability of these correlations is puzzling because in vitro adjustments of plasma levels of GlcCer in pooled normal plasma affect the anticoagulant response to APC:protein S.

Because GlcCer is a minor lipid component of all classes of plasma lipoproteins, it is possible that one or more minor apolipoproteins also play functional roles in the expression of APC/protein S anticoagulant activity in conjunction with plasma GlcCer. If so, one wonders what are the effects on plasma lipoproteins of the in vitro manipulations that alter GlcCer levels. Since the metabolism of GlcCer is linked to that of other plasma neutral glycolipids, eg., Gb3Cer, that could also affect anticoagulant response, correlations might preferably be sought between anticoagulant response and the combined plasma levels of GlcCer and Gb3Cer. Finally, plasma GlcCer low levels might reflect defects in cellular GlcCer availability that relates to cell-dependent antithrombotic mechanisms that affect risks of thrombosis.

Our observations that two neutral glycolipids, GlcCer and Gb3Cer, can influence the anticoagulant action of APC:protein S and that low plasma GlcCer is a potential risk factor for venous thrombosis provide the surprising implication that neutral glycolipids may influence blood coagulation reactions. (17) It is widely recognized that activation of the blood coagulation system is enhanced by charged phospholipid membrane surfaces as is the expression of the anticoagulant protein C pathway. However, procoagulant and anticoagulant complexes may be differently affected by different membrane phospholipid components or lipoproteins. For instance, the anionic phospholipid, phosphatidylserine very effectively enhances prothrombin activation by factor Xa:factor Va complexes. VLDL can potentially support prothrombinase activity (35–37) whereas HDL, particularly HDL2 (Deguchi, Fernandez and Griffin, unpublished data), can act as an anticoagulant cofactor by enhancing protein S-dependent APC activity. (21) Thus, the blood coagulation pathways and the counterbalancing protein C anticoagulant system can be differentially modulated by various lipids and lipoproteins. Studies presented here raise the possibility that any number of the several hundred glycolipids might contribute to up-regulation or down-regulation of thrombin generation.

The ability of GlcCer and Gb3Cer to modulate plasma's sensitivity to APC:protein S may be clinically relevant. Pregnancy and oral contraceptive usage reduce the anticoagulant response to APC. (8, 38, 39) Estradiol lowers GlcCer synthase, the primary enzyme that synthesizes GlcCer, and it also raises glucosidase activity (40) suggesting plasma GlcCer levels might be reduced by pregnancy or oral contraceptive use. Some anti-cancer drugs are also known to reduce GlcCer synthesis, (41, 42) and tamoxifen decreases GlcCer synthesis in cultured cells. (42) Since tamoxifen use is also associated with increase risk of venous thrombosis, (43) lowered GlcCer may reduce the sensitivity of tamoxifen-treated patients to APC:protein S and thereby increase risk of venous thrombosis.

The importance of vascular-bed specific signals and molecules as risk factors for vascular-bed specific thrombosis has been recently highlighted. (44) Given the possibility for vascular-bed specific expression of any number of several hundred glycolipids, it is tempting to speculate that tissue-bed specific glycolipids may modulate both procoagulant and anticoagulant reactions. For example, negatively charged sulfatides can exert both procoagulant and anticoagulant activities. (45, 46) Thus, there are a number of intriguing implications of the observation that the neutral glycolipids, GlcCer and Gb3Cer, enhance APC:protein S anticoagulant response and that a low level of plasma GlcCer appears to be a potential risk factor for venous thrombosis.

REFERENCES

1. Svensson P J, Dahlbäck B: Resistance to activated protein C as a basis for venous thrombosis. N Engl J Med. 1994;330:517–522.
2. Sakata T, Kario K, Katayama Y, Matsuyama T, Kato H, Miyata T. Clinical significance of activated protein C resistance as a potential marker for hypercoagulable state. Thromb Res. 1996;82;235–244.
3. Rodeghiero F, Tosetto A. Activated protein C resistance and factor V Leiden mutation are independent risk factors for venous thromboembolism. Ann Intern Med. 1999;130:643–650.
4. de Visser M C, Rosendaal F R, Bertina R M. A reduced sensitivity for activated protein C in the absence of factor V Leiden increases the risk of venous thrombosis. Blood. 1999;93:1271–1276.
5. Bertina R M, Koeleman B P, Koster T, et al. Mutation in blood coagulation factor V associated with resistance to activated protein C. Nature. 1994;369:64–67.
6. Greengard J S, Sun X, Xu X, Fernández J A, Griffin J H, Evatt B. Activated protein C resistance caused by Arg506Gln mutation in factor Va. Lancet. 1994;343:1361–1362.
7. Voorberg J, Roelse J, Koopman R, et al. Association of idiopathic venous thromboembolism with single point-mutation at Arg506 of factor V. Lancet. 1994;343:1535–1536.
8. Rosing J, Middeldrop S, Curvers J, et al. Low-dose oral contraceptives and aquired resistance to activated protein C. Lancet. 1999;354:2036–2040.
9. Zivelin A, Gitel S, Griffin J H, et al. Extensive venous and arterial thrombosis associated with an inhibitor to activated protein C. Blood. 1999;94:895–901.
10. Fisher M, Fernández J A, Ameriso S F, et al. Activated protein C resistance in ischemic stroke not due to factor V arginine506—>glutamine mutation. Stroke. 1996;27:1163–1166.
11. van der Bom J G, Bots M L, Haverkate F, et al. Reduced response to activated protein C is associated with increased risk for cerebrovascular disease. Ann Intern Med. 1996;125:265–269.
12. Branson H E, Katz J, Marble R, Griffin J H. Inherited protein C deficiency and coumarin-responsive chronic relapsing purpura fulminans in a newborn infant. Lancet. 1983;2:1165–1168.
13. Seligsohn U, Berger A, Abend M, et al. Homozygous protein C deficiency manifested by massive venous thrombosis in the newborn. N Engl J Med. 1984;310:559–562.
14. Mahasandana C, Suvatte V, Marlar R A, Manco-Johnson M J, Jacobson L J, Hathaway W E. Neonatal purpura fulminans associated with homozygous protein S deficiency. Lancet. 1990;335:61–62.
15. Jalbert L R, Rosen E D, Moons L, et al. Inactivation of the gene for anticoagulant protein C causes lethal perinatal consumptive coagulopathy in mice. J Clin Invest. 1998;102:1481–1488.
16. Marlar R A, Kleiss A J, Griffin J H. Mechanism of action of human activated protein C, a thrombin-dependent anticoagulant enzyme. Blood. 1982;59:1067–1072.
17. Davie E W, Fujikawa K, Kisiel W. The coagulation cascade: initiation, maintenance, and regulation. Biochemistry. 1991;30:10363–10370.
18. Smirnov M D, Esmon C T. Phosphatidylethanolamine incorporation into vesicles selectively enhances factor Va inactivation by activated protein C. J Biol Chem. 1994;269:816–819.
19. Smirnov M D, Ford D A, Esmon C T, Esmon N L. The effect of membrane composition on the hemostatic balance. Biochemistry. 1999;38:3591–3598.
20. Fernández J A, Kojima K, Petaja J, Hackeng T M, Griffin J H. Cardiolipin enhances protein C pathway anticoagulant activity. Blood Cells Mol Dis. 2000;26:115–23.
21. Griffin J H, Kojima K, Banka C L, Curtiss L K, Fernandez J A. High-density lipoprotein enhancement of anticoagulant activities of plasma protein S and activated protein C. J Clin Invest. 1999;103:219–227.
22. Dawson G, Kruski A W, Scanu A M. Distribution of glycosphingolipids in the serum lipoproteins of normal human subjects and patients with hypo- and hyperlipidemias. J Lipid Res. 1976;17:125–131.
23. Hakomori S, Igarashi Y. Functional role of glycosphingolipids in cell recognition and signaling. J Biochem. 1995; 118:1091–1103.
24. Skipski V P, Barclay M, Barclay R K, Fetzer V A, Good J J, Archibald F M. Lipid composition of human serum lipoproteins. Biochem J. 1967;104:340–352.
25. Deguchi H, Fernández J A, Hackeng T M, Banka C L, Griffin J H. Cardiolipin is a normal component of human plasma lipoproteins. Proc Natl Acad Sci USA. 2000;97:1743–1748.
26. Kundu S K. Thin-layer chromatography of neutral glycosphingolipids and gangliosides. Methods Enzymol. 1981;72:185–204.
27. Wilkening G, Linke T, Sandhoff K. Lysosomal degradation on vesicular membrane surfaces. Enhanced glucosylceramide degradation by lysosomal anionic lipids and activators. J Biol Chem. 1998; 273:30271–30278
28. Clarke J T. The glycosphingolipids of human plasma lipoproteins. Can J Biochem. 1981;59:412–417.
29. Chatterjee S. Sphingolipids in atherosclerosis and vascular biology. Arterioscler Thromb Vasc Biol. 1998;18:1523–1533.
30. Kalafatis M, Rand M D, Mann K G. The mechanism of inactivation of human factor V and human factor Va by activated protein C. J Biol Chem. 1994;269:31869–31880.
31. Rosing J, Hoekema L, Nicolaes M C, et al. Effects of protein S and factor Xa on peptide bond cleavages during inactivation of factor Va and factor VaR506Q by activated protein C. J Biol Chem. 1995;270:27852–27858.
32. Solymoss S, Tucker M M, Tracy P B. Kinetics of inactivation of membrane-bound factor Va by activated protein C. Protein S modulates factor Xa protection. J Biol Chem. 1988;263:14884–14890.
33. Heeb M J, Kojima Y, Hackeng T M, Griffin J H. Binding sites for blood coagulation factor Xa and protein S involving residues 493–506 in factor Va. Protein Sci. 1996;5:1883–1889.
34. Thorelli E, Kaufman R J, Dahlback B. Cleavage of factor V at Arg506 by activated protein C and expression of anticoagulant activity of factor Va. Blood. 1999;93:2552–2558.
35. Bradley W A, Gianturco S H. Vitamin K-dependent proteins bind to very low-density lipoproteins. Semin Thromb Hemost. 1988;14:253–257.
36. Moyer M P, Tracy R P, Tracy P B, van't Veer C, Sparks C E, Mann K G. Plasma lipoproteins support prothrombinase and other procoagulant enzymatic complexes. Arterioscler Thromb Vasc Biol. 1998;18:458–465.
37. Xu N, Dahlbäck B, Ohlin A K, Nilsson A. Association of vitamin K-dependent coagulation proteins and C4b binding protein with triglyceride-rich lipoproteins of human plasma. Arterioscler Thromb Vasc Biol. 1998; 18:33–39.
38. Curvers J, Thomassen M C, Nicolaes G A, et al. Acquired APC resistance and oral contraceptives: differences between two functional tests. Br J Haematol. 1999; 105:88–94.
39. Cumming A M, Tait R C, Fildes S, Young A, Keeney S, Hay C R. Development of resistance to activated protein C during pregnancy. Br J Haematol. 1995;90:725–727.
40. Shukla A, Shukla G S, Radin N S. Control of kidney size by sex hormones: possible involvement of glucosylceramide. Am J Physiol. 1992;262:F24–F29.
41. Radin N S. Chemotherapy by slowing glucosphingolipid synthesis. Biochem Pharmacol 1999;57:589–595.
42. Cabot M C, Giuliano A E, Volner A, Han T Y. Tamoxifen retards glycosphingolipid metabolism in human cancer cells. FEBS Lett. 1996;394:129–131.
43. Meier C R, Jick H. Tamoxifen and risk of idiopathic venous thromboembolism. Br J Clin Pharmacol. 1998;45:608–612.
44. Rosenberg R D, Aird W C. Vascular-bed specific hemostasis and hypercoagulable states. N Engl J Med. 1999;340:1555–1564.
45. Tans G, Rosing J, Griffin J H. Sulfatide-dependent autoactivation of human blood coagulation factor XII (Hageman factor). J Biol Chem. 1983;258:8215–8222.
46. Hara A, Kutsukaka Y, Uemura K, Taketomi T. Anticoagulant activity of sulfatide and it antithrombotic effect in rabbit. J Biochem. 1993;113:781–785.
47. Bernard G R, Vincent J-L, Laterre P-F, LaRosa S P, Dhainaut J-F, Lopez-Rodriguez A, Steingrub J S, Garber J E, Helterbrand J D, Ely E W, Fisher C J Jr., for the Recombinant Human Activated Protein C Worldwide Evaluation in Severe Sepsis (PROWESS) Study Group. Efficacy and Safety of Recombinant Human Activated Protein C for Severe Sepsis. *New Engl J Med.* 2001;344:699–709.
48. *Biochemical Pathways: An Atlas of Biochemistry and Molecular Biology.* Michal G. (ed). John Wiley & Sons Inc. New York, 1999. (pp. 165–166)
49. Lehninger A L. *Principles of Biochemistry.* Anderson S. and Fox J.(eds). Worth Publishers Inc. New York, 1986. (pp.277–287).

We claim:

1. A method of determining an individual at risk for thrombosis comprising:
   a) measuring a level of neutral glycolipid in a test biological specimen obtained from an individual;
   b) comparing the level of said neutral glycolipid in said test biological specimen to a normal range of neutral glycolipid in a normal biological specimen, wherein a lower level of neutral glycolipid in the test biological specimen is indicative of a risk for thrombosis for the individual.

2. The method according to claim 1, wherein the biological specimen is plasma, serum, urine, cerebrospinal fluid, semen, lung fluid, lymph, saliva, or urine.

3. The method according to claim 1, wherein the thrombosis is venous thrombosis or arterial thrombosis.

4. The method according to claim 1, wherein the neutral glycolipid is selected from the group consisting of glucosylceramide, globotriaosylceramide, and lactosylceramide.

5. The method according to claim 1, wherein a lower level of neutral glycolipid is: below the $15^{th}$ percentile of the normal range of neutral glycolipid from a normal biological specimen, or below the $10^{th}$ percentile of the normal range of neutral glycolipid from a normal biological specimen.

6. A method of determining an individual at risk for thrombosis comprising:
   A) measuring a level of glucosylceramide in a test biological specimen obtained from an individual;
   B) comparing the level of said glucosylceramide to a normal range of glucosylceramide from a biological specimen, wherein a lower than normal level of glucosylceramide in the test biological specimen compared to a mean normal range in a normal biological specimen is indicative of a risk for thrombosis for the individual.

7. The method according to claim 1, wherein the biological specimen is plasma, serum, cerebrospinal fluid, semen, lung, saliva, fluid, lymph or urine.

8. The method according to claim 1, wherein the thrombosis is venous thromobosis or arterial thrombosis.

9. The method according to claim 1, wherein the mean normal range of glucosylceramide is about 6.0 to about 7.0 µg/ml, and wherein the biological specimen is plasma.

10. The method according to claim 1, wherein a lower than normal level of glucosylceramide is about 4.6 µg/ml or less in plasma or about 4.2 µg/ml or less in plasma.

11. The method according to claim 6, wherein a lower level of glucosylceramide is: below the $15^{th}$ percentile of the normal range; or below the $10^{th}$ percentile of the normal range.

12. The method according to claim 6, further comprising chromatographic separation of said biological specimen into component parts, wherein said chromatographic separation comprises high performance liquid chromatography, thin layer chromatography, paper chromatography, gas chromatography, affinity chromatography, or affinity chromatography utilizing an antibody or antigen binding fragment thereof.

* * * * *